US012788715B2

(12) United States Patent
Sznitman et al.

(10) Patent No.: US 12,788,715 B2
(45) Date of Patent: Nov. 10, 2026

(54) METHOD FOR PULMONARY FOAM DELIVERY

(71) Applicant: TECHNION RESEARCH & DEVELOPMENT FOUNDATION LIMITED, Haifa (IL)

(72) Inventors: Josue Sznitman, Haifa (IL); Yan Ostrovski, Beer-Sheva (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 19/637,911

(22) Filed: Apr. 2, 2026

(65) Prior Publication Data

US 2026/0232580 A1 Aug. 13, 2026

Related U.S. Application Data

(60) Continuation of application No. 18/971,872, filed on Dec. 6, 2024, which is a division of application No.
(Continued)

(30) Foreign Application Priority Data

Nov. 6, 2016 (IL) .......................................... 248775

(51) Int. Cl.
*A61M 3/02* (2006.01)
*A61K 9/00* (2006.01)
(Continued)

(52) U.S. Cl.
CPC .............. *A61K 9/007* (2013.01); *A61K 9/122* (2013.01); *A61K 35/42* (2013.01); *A61M 13/003* (2013.01);
(Continued)

(58) Field of Classification Search
CPC ........ A61K 9/007; A61K 9/122; A61K 35/42; A61M 13/003; A61M 16/14;
(Continued)

(56) References Cited

U.S. PATENT DOCUMENTS 7,025,290 B2 4/2006 Harman et al.
2002/0058009 A1 5/2002 Bartus et al.
(Continued)

FOREIGN PATENT DOCUMENTS

CN 203139358 U 8/2013
JP 2020503371 A 1/2020
(Continued)

OTHER PUBLICATIONS

Abdula, "Bubbling and foaming assisted clearing of mucin plugs in microfluidic Y-junctions", Journal of Biomechanics, Nov. 2017, 7;64: pp. 1-7. Retrieved Jul. 19, 2021 from http://dx.doi.org/10.1016/j. biomech.2016.04.028.
(Continued)

*Primary Examiner* — Wesley G Harris
*Assistant Examiner* — Charles W Nichols
(74) *Attorney, Agent, or Firm* — GREENBERG TRAURIG, LLP

(57) ABSTRACT

The invention, provides a method and a device for delivery of foam to a target site of a respiratory system of a subject.

19 Claims, 12 Drawing Sheets

Related U.S. Application Data

16/347,647, filed as application No. PCT/IL2017/051208 on Nov. 6, 2017, now abandoned.

(51) Int. Cl.

| | |
|---|---|
| ***A61K 9/12*** | (2006.01) |
| ***A61K 35/42*** | (2015.01) |
| ***A61M 1/00*** | (2006.01) |
| ***A61M 13/00*** | (2006.01) |
| ***A61M 16/10*** | (2006.01) |
| ***A61M 16/14*** | (2006.01) |
| *A61M 31/00* | (2006.01) |

(52) U.S. Cl.

CPC ........ *A61M 16/1005* (2014.02); *A61M 16/14* (2013.01); *A61M 31/00* (2013.01); *A61M 2202/0208* (2013.01); *A61M 2202/0488* (2013.01); *A61M 2205/3334* (2013.01); *A61M 2205/3379* (2013.01); *A61M 2210/1035* (2013.01); *A61M 2210/1039* (2013.01)

(58) Field of Classification Search

CPC .............. A61M 16/1005; A61M 31/00; A61M 2202/0208; A61M 2202/0488; A61M 2205/3334; A61M 2205/3379; A61M 2210/1035; A61M 2210/1039; A61M 35/006; A61M 1/00

See application file for complete search history.

(56) References Cited

U.S. PATENT DOCUMENTS

| | | | | |
|---|---|---|---|---|
| 2002/0147462 | A1* | 10/2002 | Mair ................ | A61B 17/12022 604/82 |
| 2003/0228344 | A1 | 12/2003 | Fields et al. | |
| 2006/0280690 | A1* | 12/2006 | Wright .................... | A61P 41/00 128/200.23 |
| 2008/0274060 | A1 | 11/2008 | Wright et al. | |
| 2014/0242064 | A1* | 8/2014 | Morriss ................ | A61K 9/0043 424/94.67 |
| 2014/0271531 | A1 | 9/2014 | Freyman et al. | |
| 2015/0196682 | A1* | 7/2015 | Tsai ...................... | A61K 38/38 514/15.2 |
| 2018/0078119 | A1 | 3/2018 | Krimsky | |

FOREIGN PATENT DOCUMENTS

| | | |
|---|---|---|
| WO | 0072821 | 12/2000 |
| WO | 2008124500 A1 | 10/2008 |
| WO | 2008141059 A2 | 11/2008 |
| WO | 2017187438 A1 | 11/2017 |

OTHER PUBLICATIONS

Anzueto et al., "Aerosolized Surfactant In Adults With Sepsis-Induced Acute Respiratory Distress Syndrome", The New England Journal of Medicine, vol. 334, No. 22, May 30, 1996, pp. 1417-1421; Retrieved May 6, 2013 from nejm.org. DOI: 10.1056/NEJM199605303342201.

PCT International Search Report and Written Opinion for International Application No. PCT/IL2017/051208, mailed Mar. 5, 2018.

* cited by examiner

METHOD FOR PULMONARY FOAM DELIVERY

CROSS-REFERENCE TO RELATED APPLICATIONS

This application is a continuation of U.S. patent application Ser. No. 18/971,872, filed on Dec. 6, 2024, which is a divisional of U.S. patent application Ser. No. 16/347,647, filed on May 6, 2019, which is a national phase filing under 35 USC 371 of International Application No. PCT/IL2017/051208, filed on Nov. 6, 2027, which claims the benefit of priority of Israel Patent Application No. 248775, filed on Nov. 6, 2016. The contents of all of the above applications are incorporated by reference in their entirety as if fully set forth herein.

FIELD OF INVENTION

The present invention, in some embodiments thereof, is directed to pulmonary delivery of foams.

BACKGROUND OF THE INVENTION

The lungs can be described as a dense tree, where the airways resemble branches, ending with raspberry-like acinar sacs. The acinar sacs are made of alveoli, the basic respiratory units of the lungs. The alveolar lumen is composed of a confluent layer of alveolar epithelial cells where the underlying alveolar wall membrane is perfused by a vast network of capillaries. The main function of the lungs is undertaken within the alveolar space with the exchange of oxygen and carbon dioxide.

The lungs constitute the largest non-invasive pathway for drug delivery, with an exchange surface estimated at over 100 $m^2$ in an average adult. This pathway is particularly attractive for treating lung diseases topically, including lung cancer, asthma and obstructive diseases (e.g., COPD).

To treat lung diseases that affect the alveolar region, (e.g. pneumonia) therapeutics can be delivered systemically, in which case only small fraction of the drug reaches the site of the disease, i.e. within alveoli.

In lung diseases such as acute respiratory distress syndrome (ARDS), surfactant needs to be delivered in very large doses to the alveoli. This is done with some success in neonates using liquid instillation. Yet, there is currently no way to administer sufficient doses of surfactant in a uniform manner directly into the lungs.

One of the main treatment paths for upper airway related diseases is aerosol therapy. This therapy suffers from many drawbacks, e.g., only very small doses of inhaled particles can be targeted to the airways. Moreover, aerosols cannot always be inhaled in cases of severe narrowing, e.g. Severe Asthma attack.

In many cases the lungs are filled with excess material that is interfering with normal gas exchange, some examples include pulmonary alveolar proteinosis (PAP), acute pneumonia, edema, ARDS, following liquid ventilation (e.g. with perfluorocarbon), inhaled chemicals, asbestos and other fibers etc. Today, the lungs are repeatedly filled with saline and emptied, until the collected fluid is clear (the standard treatment in PAP is saline wash). The problem underlying this method is the lungs are difficult to empty, with large volumes of saline being left inside the lungs.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The present invention, in some embodiments thereof, is directed to pulmonary delivery of foams.

According to a first aspect, the invention provides a method for delivering a composition to a target site of a respiratory system of a subject, the method comprising the steps of i. providing a composition comprising a liquid foam;

ii. introducing the composition to a first site of the respiratory system, wherein the first site is proximal to the target site; and iii. introducing a predefined volume of gas, into the respiratory system to push the composition from the first site into the target site of the respiratory system, thereby delivering the composition to the target site.

In some embodiments, the method comprises a preliminary step of subjecting the subject to pre-oxygenation.

In some embodiments, the composition is delivered to one or more target sites within the respiratory system of the subject. In some embodiments, the composition is delivered simultaneously to each of the one or more target sites. In some embodiments, the composition is delivered sequentially to each of the one or more target sites.

In some embodiments, the first site is selected from the group consisting of: trachea, right main bronchus, left main bronchus, right lobar (secondary) bronchi, left lobar bronchi, any one of the segmental (tertiary), any one of the conducting bronchioles, any one of the terminal bronchioles, and any combination thereof.

In some embodiments, the target site is selected from the group consisting of: right lung, left lung, and a combination thereof. In some embodiments, the target site is selected from the group consisting of: trachea bronchi of the right lung, bronchioles of the right lung, alveolar ducts of the right lung, alveoli of the right lung, alveolar sacs of the right lung, capillary of the right lung, bronchi of the left lung, bronchioles of the left lung, alveolar ducts of the left lung, alveoli of the left lung, alveolar sacs of the left lung, capillary of the left lung and any combination thereof.

In some embodiments, the at least one of the introduction of steps (ii) and (iii) is performed in a controllable manner. In some embodiments, the introduction is performed by using a device selected from the group consisting of: bronchoscope, a catheter, a tube, a nasotracheal tube, and an orthotracheal tube.

In some embodiments, the composition is delivered to the respiratory system in a rate of 3 to 9 liter per min.

In some embodiments, the liquid foam is transformed into liquid within a predefined time range.

In some embodiments, the predefined time range is 1 second to 60 minutes within the target site. In some embodiments, the foam has a half-life of 0.5 seconds to 30 minutes within the target site. In some embodiments, the half-life is under a temperature range of 35 to 40 degrees Celsius. In some embodiments, the half-life is under a pressure range of 50 to −20 $cmH_2O$ gage.

In some embodiments, the transformation/breakdown of the liquid foam into liquid is induced by at least one method selected from the group consisting of: acoustic waves, and high frequency oscillatory ventilation (HFOV). In some embodiments, the transformation/breakdown is induced by a method comprising the step of: contacting the composition with a predefined volume of gas comprising a de-foaming agent to induce breakdown of the liquid foam. In some embodiments, the contacting is performed in the target site.

In some embodiments, the liquid foam has a viscosity ranges between 0.01 to 1 (Pascal·Math·second) Pa·Math·s. In some embodiments, a liquid constitutes between 2% to 30% of the liquid foam. In some embodiments, the liquid foam comprises gas bubbles having an average diameter size of 5 m-5 mm.

In some embodiments, the composition further comprises one or more active agents. In some embodiments, the one or more active agents constitute between 0.01% to 100% of a liquid fraction of the foam. In some embodiments, the one or more active agents are selected from the group consisting of: therapeutic agent, prophylactic agent and diagnostic agent. In some embodiments, the one or more active agents are selected from the group consisting of: a protein, a peptide, a nucleic acid, a small molecule, a lipid, a glycolipid, a cell, and an antibody. In some embodiments, the one or more active agents are selected from the group consisting of: a surfactant, a cytotoxic agent, an antineoplastic agent, a chemotherapeutic agent, anti-metastatic agent, a hormone, a steroid, a bronchodilator, an anticoagulant, an immune-modulating agent, a β-agonist, an antibiotic, antifungal agent, anti-bacterial and an antiviral agent. In some embodiments, the one or more active agents comprise cells (e.g., stem cells).

In some embodiments, the liquid foam is loaded with stem cells, and wherein the disease is selected from the group consisting of: a chronic obstructive pulmonary disease (COPD), an idiopathic pulmonary fibrosis (IPF), an acute respiratory distress syndrome (ARDS).

In some embodiments, the method further comprises a step of pulling back at least partial amount of the liquid foam from the target site of the respiratory system.

According to a second aspect, the invention provides a pulmonary drug delivery device configured to provide a liquid foam to a target site of a respiratory system of a subject.

In some embodiments, pulmonary drug delivery device comprises:

- a first compartment configured to provide a liquid foam; and
- an elongated hollow tube having (i) a proximal end configured to receive the liquid foam, so that the liquid foam is pushed therein; and (ii) a distal end configured to insert the foam into the target site of the respiratory system of the subject. In some embodiments, the distal end is sized and shaped to attach to the respiratory system of the subject, so that the liquid foam is directly injected to the respiratory system.

In some embodiments, the pulmonary drug delivery device, further comprises a second compartment configured to provide a pressurized gas, wherein the gas pushes the liquid foam into the target site of the respiratory system.

In some embodiments, an outlet of the first compartment is sized and shaped to attach to a proximal site of the target site of the respiratory system. In some embodiments, the first compartment is further configured to pull back at least partial amount of the liquid foam from the target site of the respiratory system.

In some embodiments, the pulmonary drug delivery device further comprises a control unit adapted to control one or more parameters selected from the group consisting of: a flow rate of the liquid foam in the elongated hollow tube, and the amount of the liquid foam inserted into the respiratory system.

In some embodiments, the pulmonary drug delivery device, further comprises a control unit adapted to control one or more parameters selected from the group consisting of: a flow rate of the liquid foam in the elongated hollow tube, a flow rate of the gas, and the amount of the liquid foam inserted into the respiratory system.

In some embodiments, the first compartment is in the form of a syringe.

In some embodiments, the first compartment further comprises an agitation element.

In some embodiments, the second compartment is selected from the group consisting of: syringe and a ventilation machine.

In some embodiments, the liquid foam further comprises or has incorporated thereto, one or more active agents.

In some embodiments, the pulmonary drug delivery device is for use in a method of treatment of a lung disease in a subject.

In some embodiments, the disease is acute respiratory distress syndrome (ARDS).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the Drawings.

DETAILED DESCRIPTION OF THE INVENTION

Figure 1A:
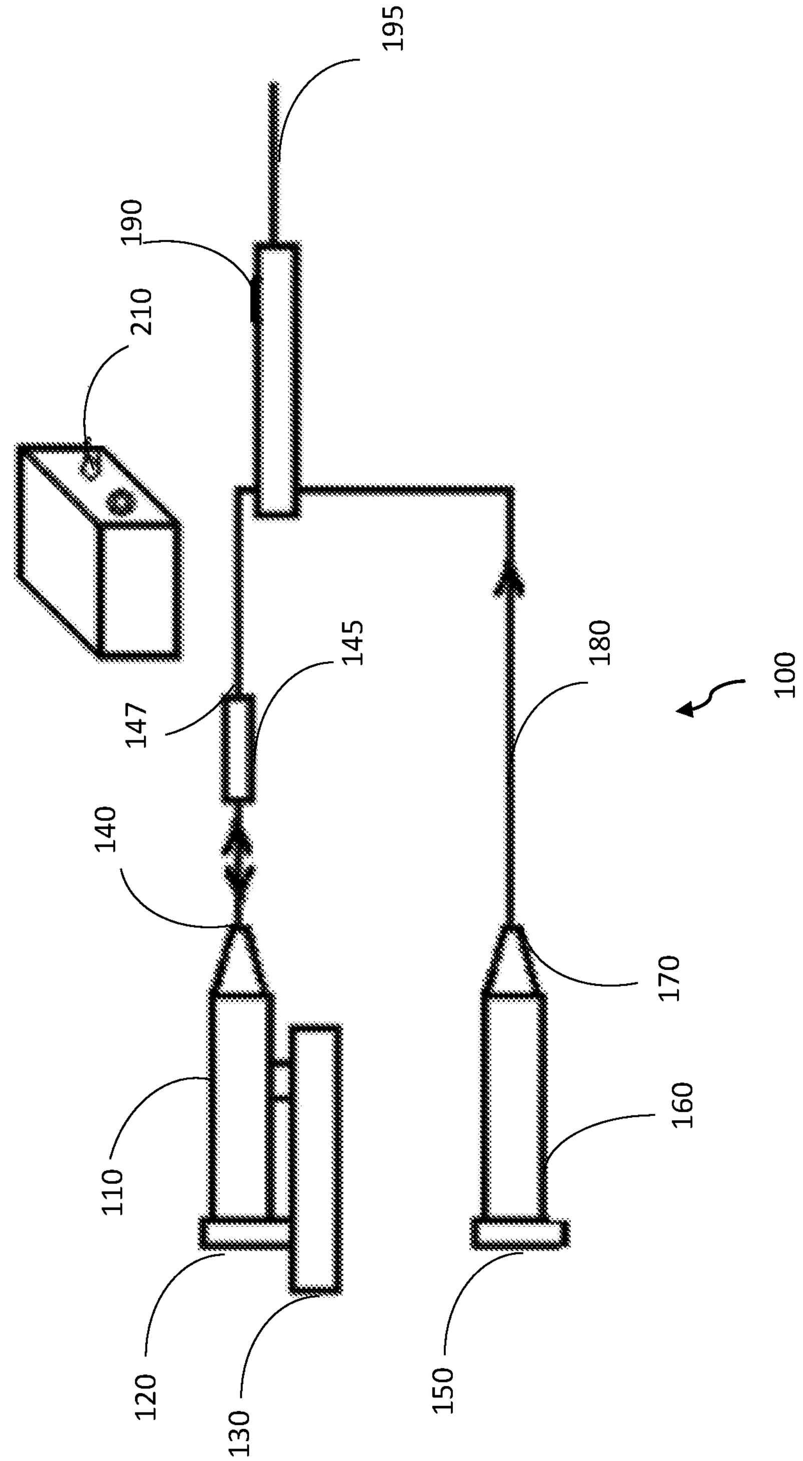
FIG. 1A shows a cross section of a top view of a device for pulmonary delivery of liquid foams in accordance to some embodiments of the disclosure.

The present invention provides, in some embodiments, foam for pulmonary delivery, and method of use thereof. In some embodiments, the foam is a pulmonary delivery vehicle which facilitates delivery of one or more active agents/drugs into the pulmonary system. In some embodiments, the invention provides pharmaceutical foam compositions for pulmonary administration. In some embodiments, the invention provides methods for delivering compositions comprising foam into the respiratory system of a subject.

The present invention is based, in part, on the discovery that foam acts as an attractive drug carrier for pulmonary delivery or may act as the active agent itself. Moreover, the compositions and methods described herein enable high deposition of active agents such as drugs.

Advantageously, foam pulmonary delivery, rather than liquid or aerosol, allows a more uniform distribution, optionally of large doses, within the respiratory system.

According to some embodiments, the invention provides a method for delivering a composition to a target site of a respiratory system of a subject, the method comprising the steps of (i) providing a composition comprising a liquid foam; (ii) introducing the composition to a first site of the respiratory system, wherein the first site is proximal to the target site; and (iii) introducing a predefined volume of gas, into the respiratory system to push the composition from the first site into the target site of the respiratory system, thereby delivering the composition to the target site.

In some embodiments, the introducing a predefined volume of gas, is performed by the subject's voluntary lung expansion. In a non-limiting embodiment, the foam is pulled distally from the first site, into the target site, by the subject's voluntary lung expansion, thereby delivering the composition to the target site.

In some embodiments, the method further comprises a preliminary step of subjecting the subject to pre-oxygenation.

As used herein, the term "pre-oxygenation" refers to an administration of oxygen to a subject to reach an oxygen level exceeding a normal oxygen level prior to intubation so to extend the safe apnea time. Maximal pre-oxygenation is achieved when the alveolar, arterial, tissue, and venous compartments are all filled with oxygen. As used herein the term "safe apnea time" refers to a duration of time following cessation of breathing/ventilation until critical arterial desaturation occurs.

In some embodiments, the step of introducing the composition to a first site of the respiratory system is performed in a controllable manner. In some embodiments, the step of introducing a predefined volume of gas, into the respiratory system is performed in a controllable manner. In some embodiments, at least one of the introductions of steps (ii) and (iii) is performed in a controllable manner.

The term "subject" as used herein refers to an animal, more particularly to non-human mammals and human organism. In one embodiment, the subject is a human. Human subjects may also include neonates and prematurely born neonates.

A skilled artisan would appreciate that a variety of commercially available devices may be suitable for introducing the composition of the invention. Non-limiting example of devices suitable for introducing the composition of the invention include a bronchoscope, a catheter, a tube, a nasotracheal tube, and an orthotracheal tube. Further non-limiting examples of the device are described herein under "Applications and Method".

In some embodiments, the first site is in an upper airway within a respiratory system of a subject. In some embodiments, the first site is selected from the group consisting of trachea, right main bronchus, left main bronchus, right lobar (secondary) bronchi, left lobar bronchi, any one of the segmental (tertiary), any one of the conducting bronchioles, any one of the terminal bronchioles, and any combination thereof.

In embodiments wherein the first site is distal to the trachea, the subject may be able to breath during and/or immediately following the treatment. Advantageously, in such embodiments risks associated with cessation of breathing are avoided.

In some embodiments, the composition is delivered to one or more target sites within the respiratory system of the subject. In some embodiments, the composition is delivered simultaneously to each of the one or more target sites. In some embodiments, the composition is delivered sequentially to each of the one or more target sites.

In some embodiments, the target site is selected from: right lung, left lung, and a combination thereof. In some embodiments, the target site is selected from: trachea bronchi of the right lung, bronchioles of the right lung, alveolar ducts of the right lung, alveoli of the right lung, alveolar sacs of the right lung, capillary of the right lung, bronchi of the left lung, bronchioles of the left lung, alveolar ducts of the left lung, alveoli of the left lung, alveolar sacs of the left lung, capillary of the left lung and any combination thereof.

In some embodiments, the liquid foam within the target site is broken down within a predefined time period. A person skilled in the art would appreciate that the predefined time period may be determined according to a desired target site within the pulmonary system as well as route of administration. For a non-limiting example, when a foam is delivered simultaneously to both lungs of a subject, it requires fast break down time in order to avoid choking, hence the liquid foam inside the lungs should break into liquid within a time range of seconds to a minute.

In some embodiments, the predefined time period is less than 1 hour, less than 2 hours, less than 3 hours, less than 4 hours, less than 5 hours, less than 12 hours, or less than 24 hours. In some embodiments, the predefined time period is less than 1 minute (min), less than 2 min, less than 3 min, less than 4 min, less than 5 min, less than 10 min, less than 20 min, less than 30 min, less than 40 min, less than 50 min, or less than 60 min. Each possibility represents a separate embodiment of the present invention. In some embodiments, the predefined time period ranges between 0 to 1 min, 0 to 2 min, 0 to 3 min, 0 to 4 min, 0 to 5 min, 0 to 10 min, 0 to 20 min, 0 to 30 min, 0 to 40 min, 0 to 50 min, or 0 to 60 min. In some embodiments, the predefined time period is 1 second to 60 minutes.

The breakdown of the liquid foam to liquid may be induced by environmental conditions such as increased shear stress, increased pressure, or increased temperature. Optionally, the environmental conditions are within the respiratory system, within the target site or within the first site. Optionally, the foam may breakdown due to the narrowing of the airways distal to the site of administration. For a non-limiting example, a liquid foam may be stable in a room temperature for few days and break down to liquid when exposed to a body's temperature within few minutes. Optionally, the foam is broken through external vibrations applied to the patient's chest or body.

Optionally, the transformation/breakdown of the liquid foam into liquid is induced by at least one method selected from: acoustic waves, and high frequency oscillatory ventilation (HFOV). In some embodiments, the transformation/breakdown is induced by a method comprising the step of: contacting the composition with a predefined volume of gas comprising a de-foaming agent to induce breakdown of the foam. In some embodiments, the contacting is performed in the target site. In some embodiments, the contacting is performed in the first site. In some embodiments, the predefined volume of gas introduced to push the composition from the first site into the target site comprises the defoaming agent. In some embodiments, 1%, 5%, 10%, 20%, 30%, 40%, 50%, 60%, 70%, 80%, 90%, 99% or 100%, by volume, including any value and range therebetween, of the volume of gas comprises a de-foaming agent. Any defoaming agent which is effective in breaking or otherwise controlling foaming in aqueous media may be used. Non-limiting examples of de-foaming agents include hydrophilic particles, alcohols and fumes thereof.

Optionally, the liquid is pre-sterilized. Alternatively, the liquid is unsterilized. Optionally, the foam formed from the unsterilized liquid may be sterilized, or the unsterilized foam may be used in locations where sterility is not critical.

In some embodiments, the foam can be pre-created, or created approximately at the moment of administration. Processes for creating foams are known in the art. Non-limiting exemplary processes include, but are not limited to, cavitation of pre-injected gas, ultrasonic release of saturated gases, chemical gas releasing reaction, gas injection from a nozzle and turbulent mixing.

In some embodiments, the foam comprises an inert carrier, for carrying a drug. In some embodiments, the foam is made of one or more drugs. In some cases, the drug itself is being foamed. In some embodiments, the foam comprises a combination of a foamed drug and an inert (i.e. non-therapeutic) foam.

Applications and Method

In some embodiments, the invention provides a composition for use in delivering a therapeutic agent or a diagnosing agent to the respiratory system. In some embodiments, the invention provides a method for delivering a therapeutic agent and/or a diagnostic agent to the respiratory system (also referred to as: "treatment procedure"). In some embodiments, the invention provides a method for treating diseases of the respiratory system. In some embodiments, the invention provides a composition for use in the treatment of diseases of the respiratory system.

In some embodiments, the disclosed method comprises a step of mixing a liquid and a gas to form foam prior to the treatment procedure. Herein, by "prior to the treatment procedure", it is meant to refer, in some embodiments, to 1 sec, 30 sec, 1 min, 2 min, 3 min, 4 min, 5 min, 10 min, 30 min, 1 h, 2 h, including any value and range therebetween, prior to the treatment procedure.

Optionally, the foam is formed within a relatively short period of time, for example, in no more than about 10 seconds, or about 30 seconds, or about 60 seconds, or other smaller, intermediate or larger time periods.

Optionally, the resulting foam may be stable for a long period of time, and/or may have a larger surfaces area of the active agent (e.g., the drug) to contact the walls of the anatomical treatment area (also referred to as: "target site").

Herein, by "stable" it is meant to refer to the foam before being breakdown back into liquid.

In some embodiments, by "stable" it is meant to refer to a desired half-life as described herein.

Herein, by "long period of time" it is meant to refer to about 5 sec, 10 sec, 20 sec, 30 sec, 40 sec, 50 sec 1 min, 5 min, 1 h, 2 h, 5 h, or 10 h, including any value and range therebetween. As a non-limiting example, 10 s may be sufficient for an automatic device, and 60 s may be sufficient for a manual device.

In some embodiments, the step of mixing a liquid and a gas is performed by a device, e.g., a handheld device.

In some embodiments, there is provided a device, e.g., for medical treatment, the device comprising:

(i) a proximal end configured to accept a liquid and gas (e.g., outside a body of a subject), so that the liquid is mixed with the gas to form a foam; and (ii) a distal end configured to insert the foam into the respiratory system of the subject.

In some embodiments, the device comprises an elongated hollow tube having the proximal end for forming a foam and a distal end for inserting foam into the respiratory system of the subject. In some embodiments, the suitable devices further comprise an obstruction (e.g., a balloon) at the tip to prevent backflow of the composition.

Reference is made to FIG. 1A which is a schematic illustration of the foam formation and injection device 100. Optionally, the device is designed to produce the amount of foam required for the selected medical procedure. Optionally, the device is designed for production of foam right before bestowing the foam for injection.

Optionally, device 100 may have a first compartment. Optionally, the first compartment may be e.g., first syringe 110. For simplicity, "first compartment" and "first syringe" are used herein interchangeably. First syringe 110 may be disposable standard syringe. First syringe 110 may have inlet 120. First syringe 110 may operate mechanically. Inlet 120 may allow a predetermined amount of liquids e.g., liquid comprising active agents (e.g., drugs), liquid foam, and surfactants enter therein. Optionally, device 100 may have an agitation element 130. Agitation element 130 may be e.g., a stirrer an agitation nozzle, or an ultrasonic transmitter. Alternatively or additionally, agitation of the liquid occurs by rotation or by vibration. Optionally, agitation element 130 may be located within first syringe 110. Optionally, agitation element 130 may be located outside first syringe 110 and adjacent thereto. Agitation element 130 may be sequentially arranged along a longitudinal axis of first syringe 110 so that the liquid flows in near proximity to each of the agitation elements. Syringe 110 may allow foaming the liquid, i.e. forming a liquid foam. First syringe 110 may have outlet 140. Optionally, outlet 140 of first syringe 110 is sized and shaped to attach to a proximal site of the target site of the respiratory system. Device 100 may have a tube 147. Outlet 140 may allow the liquids exit first syringe 110 and to enter tube 147. Optionally, outlet 140 may allow the liquids or foamed liquid passing tube 147 to enter back thereto. Optionally, device 100 may have a foaming device 145, e.g., instead of agitation element 130. Foaming device 145 may allow foaming the liquid exiting first syringe 110.

Optionally, device 100 may have a second compartment. Optionally, second compartment is a second syringe 160. For simplicity, "second compartment" and "second syringe" are used herein interchangeably. Second syringe 160 may be disposable standard syringe. Second syringe 160 may have inlet 150. Inlet 150 may allow gas (e.g., air, or oxygen) to enter therein. Second syringe 160 may have outlet 170. Device 100 may have a tube 180. Outlet 170 may allow the gas exit second syringe 160 and to enter tube 180. Device 100 may have an endotracheal tube 190. Tubes 147 and 180 may be connected to each other or may constitute one tube, thereby allowing the gas to push the liquid foam to endotracheal tube 190. By "endotracheal tube" it is further meant to encompass bronchoscope, and intubation tube. Endotracheal tube 190 may allow injecting the liquid foam to a subject's body cavities e.g., airway, or alveoli.

Typically, but not exclusively, the total volume of the foam ranges from 5 ml to 3 liter. Typically, but not exclusively, the total ratio of the gas to the liquid foam is 2:1 to 1:1 (v/v).

Optionally, device 100 may have a ventilation machine instead of second syringe 160. Ventilation machine may allow to push air, similarly to syringe 160. Optionally, device 100 may have a control unit 210. Control unit 210 may be connected to device 100 via a connecting element.

Alternatively, the foam is directly injected to a first site of the respiratory system via, endotracheal tube 190. Optionally, the operation of endotracheal tube 190 may be assisted by e.g., a needle, a tube, catheter, or other lumen 195 attached to an outlet of endotracheal tube 190. Optionally, the foam may be produced in a manner that is suitable for direct injection or for its introducing into a tube (e.g., an intubation tube).

In some embodiments, the foam is directly injected in a desired flow rate of the foam at the inlet.

Control unit 210 may control one or more foam parameters determined according to clinical experiments and/or a numerical simulation of the medical substance in various body cavities.

Optionally, controlling the parameters may be achieved by one or more operating valves.

Optionally, the one or more foam parameters are determined according to the target site in which the administration is performed. As different target sites have different characteristics, such as width and/or estimated dimensions, e.g., the alveoli of the lung, the one or more foam parameters may be changed.

Control unit 210 may control, for example, the volume of foam pushed into the lungs, the desired flow rate of the foam, and the desired time duration until the foam reaches the targeted location depth. Optionally, control unit 210 provides a predefined volume of the foam e.g., by monitoring the pressure or the flow rate of the foam passing or exiting syringe 110, in the tube 195 or in the respiratory tract of a subject. Optionally, control unit 210 allows to select different foam parameters, for example, bubble size distributions of the foam, syringe's outlet pressure, flow injection flow rate, subsequent gas injection flow rate, inject dose of foam to the patient, and injected dose of subsequent gas e.g., in second syringe 160.

Optionally, Control unit 210 may also control the mixing parameters in the syringe, mixing speed, ultrasonic transducer parameters, if used (e.g., frequency etc.).

Control unit 210 may be connected (e.g., mechanically, optically, or electronically) to one or more of: tube 195, endotracheal tube 190, foaming device 145, outlet 140, outlet 170, and tube 180.

Optionally, control unit 210 operates automatically by a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 1B:
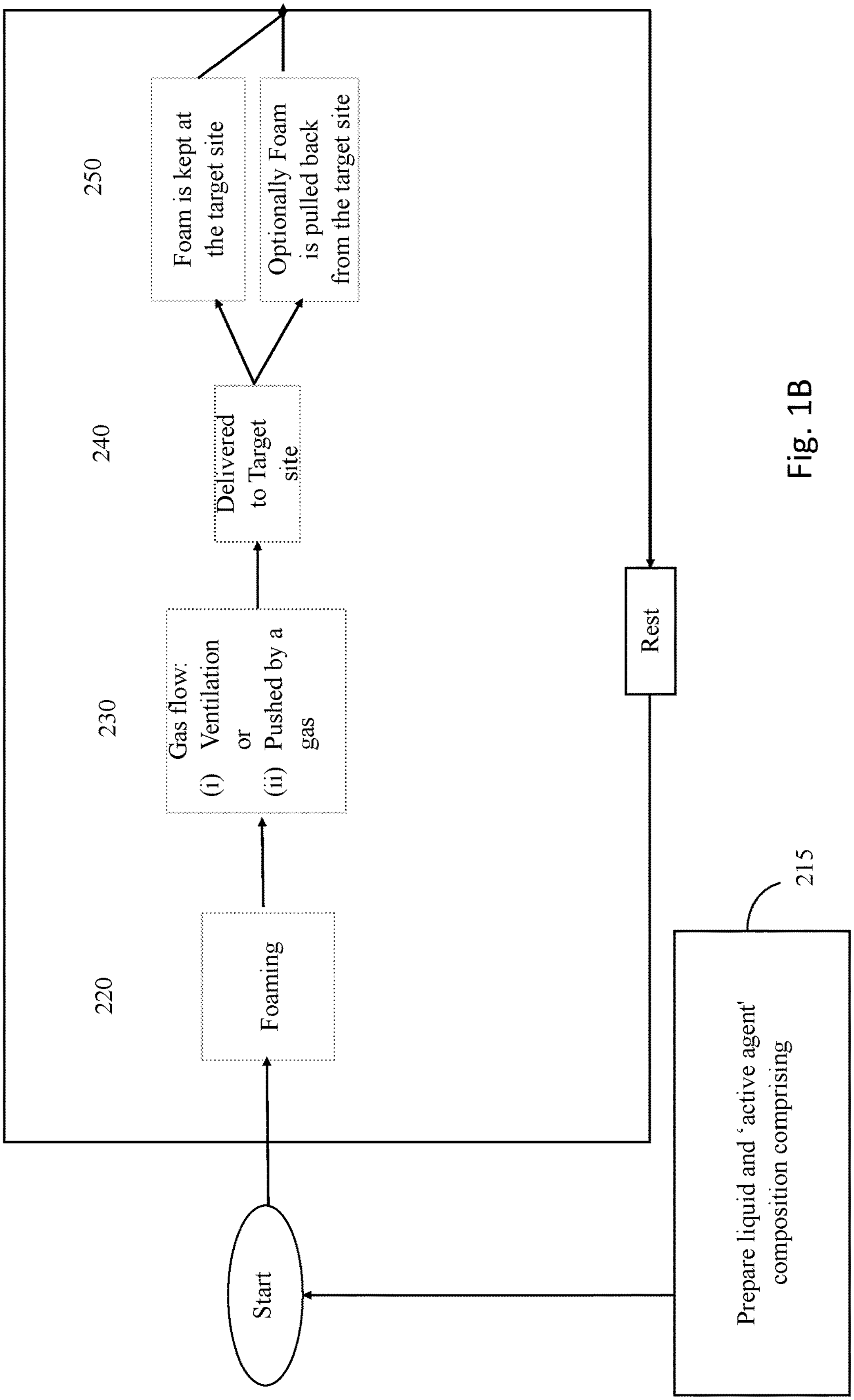
FIG. 1B is a flowchart showing the delivery of a composition to a target site of a respiratory system using a foam.

Reference is now made to FIG. 1B which is a flowchart of a non-limiting example for delivering a composition to a target site of a respiratory system described herein. A foaming step is first provided (step 220). The foam is injected to the patient's airway. The foam may comprise proteins, cells, and/or active agents as described hereinthroughout. Subsequently, a pressurized gas or ventilation machine are used (230) to push the foam into the intended treatment region, and to clear the airways for breathing or external ventilation (step 240). The foam may be pulled back out, leaving a thin residual coating on the airways (step 250). That is, a foam's dose that is as large as the anatomical dead space can be injected and pulled back, e.g., by vacuum method.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In exemplary embodiments, the desired flow rate of the foam is from 1 to 50 lit/min, e.g., about 3 to 9 lit/min, or about 6 to 10 lit/min. In some embodiments, the desired flow rate of the foam is less than 60 liter per min.

In exemplary embodiments, the desired flow rate is achieved by applying a pressure (e.g., on the device's outlet) of 1000 Pa, 2000 Pa, 3000 Pa, 4000 Pa, 5000 Pa, or 6000 Pa, including any value therebetween, e.g., as measured on the device's outlet including any value and range therebetween. In exemplary embodiments, the pressure is about 3733 Pa.

In some embodiments, the foam enters the airway is at a pressure of up to 4000 Pa (~40 $cmH_2O$).

In exemplary embodiments, the desired flow rate is obtained by pushing predefined volume of gas by applying the desired pressure, into the respiratory system so as to push the desired foam to the target site (e.g., bronchioles of a lung).

In some embodiments, the ratio of liquid to gas is in the foam about 0.3:1, about 0.5:1, about 1:1, about 1:3, about 1:6, 1:10, 1:100, or about 1:1000, including any value therebetween, or other smaller, intermediate or larger values.

For example, and without limitation, the liquid itself is the drug (e.g. surfactant delivery), and the ratio of liquid to gas is from 1:5 to 1:10.

In some embodiments, the foam is only a carrier to deliver stem cells into the alveoli, and the ratio (liquid to gas) is from 1:10 to 1:20.

In some embodiments, the foam is a carrier and it is used to deliver small amounts of large particles (e.g., >10 um), and the liquid volume fraction is minimized (1:20 to 1:100, liquid to gas).

As described hereinthroughout, in some embodiments, by "liquid" it is meant to refer to pulmonary surfactant e.g., for surfactant replacement therapy. In some embodiments, by "liquid" it is meant to refer to stem cell medium used e.g., to deliver the cells and allow them to survive. In some embodiments, by "liquid" it is meant to refer to inert carrier foam e.g., a mixture of saline and some inert protein or other surface tension reducing agent. Typically, but not exclusively, the foam is optimally physiologically inert. In some embodiments, by "liquid" it is meant to refer to local antibiotic carrier. In some embodiments, the liquid is a mixture of inert liquid (e.g. saline) and antibiotics.

In some embodiments, the diseases of the respiratory system are inflammatory and/or obstructive diseases of the respiratory system, for example, and without limitation, malignancies of the respiratory system. Non-limiting obstructive diseases include lung cancer, lung tumors, lung carcinomas, small cell lung carcinomas, throat cancer, bronchial carcinomas, larynx cancer, head/neck tumors, sarcomas and blastomas in the region or vicinity of the respiratory system, in particular the lung, as well as asthma and COPD (chronic obstructive pulmonary disease), IPF (Idiopathic pulmonary fibrosis), Ventilator associated pneumonia (VAP), lung emphysema, chronic bronchitis, pneumonia and hereditary diseases, for example mucoviscidosis, human surfactant protein B deficiency and al-antitrypsin deficiency. In some embodiments, the invention provides a composition for use for therapy after a lung transplant and for pulmonary vaccination and for anti-infective therapy of the lung. In some embodiments, the disease is acute respiratory distress syndrome (ARDS). In some embodiments, the disease is an autoimmune disease. In some embodiments, the disease is cystic fibrosis. In some embodiments, the inflammatory disease is selected from a bacterial inflammation, fungal inflammation and viral inflammation.

In some embodiments, the foam comprises an active agent (e.g., a drug), therefore the administration of foam is accompanied by the administration the drug, as described herein. In some embodiments, the administration may be assisted by using laryngeal mask, orally or nasally. In some embodiments, the foam may allow to ease these administrations, for example by reducing the viscosity of the foam. Local anesthesia can be used to further ease the administration on or by the patient.

In some embodiments, the foam can also be used to entrap liquid plugs between plugs of foam. Such method may serve to deliver some materials that could not be foamed or mixed with the foam.

In some embodiments, the invention provides a composition for use in the treatment of acute respiratory distress syndrome (ARDS). In some embodiments, the invention provides a method for treating acute respiratory distress syndrome (ARDS) in adult human. In some embodiments, the invention provides a method for treating acute respiratory distress syndrome (ARDS) in adult human. In some embodiments, the method for treating ARDS comprising introducing a foam comprising surfactant in very large doses to the alveoli, and then, in some embodiments, pulling back (i.e. cleansing) a defined amount of the foam, leaving just a coating on the airways.

In some embodiments, the invention provides a method for delivering surfactants to a subject's lungs. In some embodiments, the subject is in need of a surfactant replacement therapy. In some embodiments, the subject is a human. In some embodiments, the subject is selected from: an adult, a child, and a baby. In some embodiments, the baby is a prematurely born baby.

In some embodiments, the invention provides a composition for use in applying cells or scaffolds for being delivered uniformly throughout the lungs, or to specific diseased locations.

In some embodiments, the invention provides a composition for use in applying stem cell therapy to the respiratory system. In some embodiments, the invention provides a method for applying stem cell therapy to the respiratory system (e.g., lung). Non-limiting examples of applications of stem cell therapy to the lungs include treating hypertension, COPD, Broncho-pulmonary dysplasia (BPD), cystic fibrosis, ARDS, pulmonary fibrosis, pulmonary edema, subglottic stenosis, tracheomalacia, bronchiomalacia, emphysema and many other lung diseases. In some embodiments, the invention provides a composition for use in applying gene therapy to the respiratory system. In some embodiments, the invention provides a method for delivering gene therapy to the respiratory system (e.g., lung).

A person with skill in the art would appreciate that a portion of a liquid foam, which propagates through the airways, is at least partially deposited onto walls of the airways. This deposition of the liquid foam is dependent on the foam and administration properties (e.g., flow rate) used under the methods of the invention. Thus, in some embodiments, the foam and its administration properties may be designed to regulate its deposition onto specific regions of the airways walls. For some applications (e.g., specific drugs and lung imaging) only upper airway targeting is desired so as to refrain from allowing the active agent from reaching the blood stream and causing side effects. In such embodiments, the foam and administration properties (e.g., foam dose) may be designed such that by the time the foam reaches the acinar regions it is substantially or fully deposited on the airways walls. Alternatively, such as wherein avoiding loss of active agent in the upper airways is desired, the method comprises administering first a first foam dose devoid of an active agent, so as to coat the inner walls of the airways, and subsequently a liquid foam comprising the active agent is administered.

Some drugs that are intended for the upper airways (such as in asthma) may have adverse effects when they reach the alveoli and thus systemic circulation. This is particularly true when large drug doses are required. In some embodiments, a device may be used in a push-pull method, comprising pushing an amount of foam, approximately in a volume equal to the lungs' dead space, and then immediately pulling back (e.g., with a syringe) a define volume. As a result, a thick uniform coating of the upper airways is created without reaching the alveoli.

Compositions

In some embodiments, the invention provides a composition comprising a liquid foam that may be used for pulmonary delivery. As used herein, the term "liquid foam" refers to a physical state comprising a mass of gas bubbles in a liquid phase (e.g., water). In some embodiments, the composition is a delivery vehicle which allow or facilitate delivery of active agents/drugs via the respiratory system into the body of a subject. In some embodiments, by "gas" it is meant to refer to a mixture of a gas (e.g., air, carbon dioxide, nitrogen, oxygen).

In some embodiments, the composition is a delivery vehicle which facilitates controlled release of active agents within a target site. As used herein, the term "controlled release" refers to the ability to control the rate at which an active agent in a pharmaceutical composition of the present invention is released from its delivery vehicle under physiological conditions, such as when the drug delivery vehicle is in the lung of a subject. As a non-limiting example, the properties of the foam, such as breakdown time, provides the controlled release of active agents at a target site.

In some embodiments, the composition further comprises one or more active agents or drugs. In some embodiments, the composition is a pharmaceutical composition comprising an active agent for administration to a subject. In some embodiments, the one or more active agents or drugs are dissolved, immobilized, dispersed or suspended in the liquid phase of the foamed composition. In some embodiments, the one or more active agents constitute between 0.01% to 100% (e.g., 10%, 20%, or 30%, including any value therebetween), of the liquid fraction of the liquid foam.

In some embodiments, the composition further comprises a pharmaceutically acceptable carrier. The term "pharmaceutically acceptable carrier" refers to a carrier that may be taken into the lungs with no significant adverse toxicological effects on the lungs. Numerically, the amount may be from about 0.01% of weight to about 99.99% of weight, depending on the activity of the drug being employed. Such pharmaceutically acceptable carriers may be one or a combination of two or more pharmaceutical excipients. Non-limiting examples of pharmaceutical excipients that are useful as carriers in this invention include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two. Such pharmaceutically acceptable carriers may include one or more of: solvents, additives, excipients, dispersion media, solubilizing agents, coatings, preservatives, isotonic and absorption delaying agents, surfactants, propellants and the like that are physiologically compatible. Examples of suitable excipients include, but are not limited to: lactose, starch, propylene glycol diesters of medium chain fatty acids; triglyceride esters of medium chain fatty acids, short chains, or long chains, or any combination thereof, perfluorodimethylcyclobutane; perfluorocyclobutane; polyethylene glycol; menthol; lauroglycol; diethylene glycol monoethyl ether; polyglycolized glycerides of medium chain fatty acids; alcohols; eucalyptus oil; short chain fatty acids; and combinations thereof.

In some embodiments, the composition further comprises one or more surfactants. In some embodiments, the composition further comprises a pulmonary surfactant.

The surfactant may be manufactured by various methods. In some embodiments, the surfactant is animal derived (e.g., Beractant (Survanta), Calfactant (Infasurf), Poractant (Curosurf)), or it can be synthetic (e.g., Exosurf). In some embodiments, the surfactant is produced by cells or cell lines, e.g., alveolar type II cell lines may be used to produce and harvest surfactant. Alternatively, genetically engineered organisms or organisms created by synthetic biology methods may be used.

The term “surfactant” as used herein refers to compounds which reduce the surface tension of water when dissolved in water or aqueous solutions, or which reduce interfacial tension between two normally immiscible liquids (e.g., oil and water). Any surfactants known in the art may be used including any naturally occurring lung surfactant. Examples of suitable surfactants include, but are not limited to: oleic acid; sorbitan trioleate; cetyl pyridinium chloride; soya lecithin; polyoxyethylene(20) sorbitan monolaurate; polyoxyethylene (10) stearyl ether; polyoxyethylene (2) oleyl ether; polyoxypropylene-polyoxyethylene ethylene diamine block copolymers; polyoxyethylene(20) sorbitan monostearate; polyoxyethylene(20) sorbitan monooleate; polyoxypropylene-polyoxyethylene block copolymers; castor oil ethoxylate; and combinations thereof. More specific surfactants that may be utilized in the inhalable compositions of this invention are: oleic acid available under the trade name oleic acid NF6321 (from Henkel Corp. Emery Group, Cincinnati, Ohio); cetylpyridinium chloride (from Arrow Chemical, Inc. Westwood, N.J.); soya lecithin available under the trade name Epikuron 200 (from Lucas Meyer Decatur, 111.); polyoxyethylene(20) sorbitan monolaurate available under the trade name Tween 20 (from ICI Specialty Chemicals, Wilmington, Del.); polyoxyethylene(20) sorbitan monostearate available under the trade name Tween 60 (from ICI); polyoxyethylene(20) sorbitan monooleate available under the trade name Tween 80 (from ICI); polyoxyethylene (10) stearyl ether available under the trade name Brij 76 (from ICI); polyoxyethylene (2) oleyl ether available under the trade name Brij 92 (frown ICI); Polyoxyethylene-polyoxypropylene ethylenediamine block copolymer available under the tradename Tetronic 150 RI (from BASF); polyoxypropylene-polyoxyethylene block copolymers available under the trade names Pluronic L-92, Pluronic L-121 end Pluronic F 68 (from BASF); castor oil ethoxylate available under the trade name Alkasurf CO-40 (from Rhone-Poulene Mississauga Ontario, Canada); and mixtures thereof. These surfactants may be utilized either as the free base, as a salt, or as a clathrate (such as P-11 or hexane clathrates), depending upon the stability and solubility of the active compounds in the specific pharmaceutical composition.

In some embodiments, the term “surfactant” or “pulmonary surfactant” generally refers to specific lipoprotein substances naturally produced in the lungs that are essential for proper breathing, alveolar stability and gas exchange. Pulmonary surfactants are surface-active agents naturally formed by type II alveolar cells that reduce the surface tension at the air-liquid interface of alveoli. Pulmonary surfactants are generally made up of about 90% lipids (about half of which is the phospholipid dipalmitoylphosphatidylcholine (DPPC)) and about 10% protein. At least four native surfactants have been identified: SP-A, B, C, and D.

In some embodiments, the hydrophobic surfactant proteins B (SP-B) and C (SP-C) are tightly bound to the phospholipids, and promote their adsorption into the air-liquid interface of the alveoli. In some embodiments, these proteins are critical for formation of the surfactant film. The term “surfactant” also includes currently available surfactant preparations, including, but not limited to, Survanta® (beractant), Infasurf® (calfactant), Exosurf Neonatal® (colfosceril palmitate), Curosurf® (poractant alfa), Surfaxin® (lucinactant), Aerosurf® (aerosolized Surfaxin®), Vanticute® (lusupultide), Alveofact® (bovactant), as well as preparations being developed.

In some embodiments, the surfactant may further be selected from surface-active materials such as proteins and solution thereof.

In exemplary embodiments, the surfactant comprises albumin. For example, e.g., 2% albumin, by weight, in saline may form a stable foam.

Foams

In some embodiments, the invention provides a liquid foam. In some embodiments, the invention provides a non-newtonian foaming fluids. The liquid foam of the invention is biocompatible. As used herein, the term “biocompatible” is intended to describe materials that, are non-toxic to cells in vitro and upon administration in vivo, do not induce undesirable long-term effects. A person with skill in the art will appreciate that variety of methods may be used to generate a liquid foam. Non-limiting exemplary liquid foams which may be generated by mixing liquid with gas such as air, nitrogen, oxygen, hydrogen peroxidase, to name a few.

In some embodiments, the liquid constitutes between 1% to 50%, 1% to 40%, 1% to 30%, 1% to 20%, 2% to 50%, 2% to 40%, 2% to 30%, or 2% to 20% of the foam. In some embodiments, the liquid constitutes between 2% to 15% of the foam. Each possibility represents a separate embodiment of the present invention.

In some embodiments, the gas bubbles of the foam have a median diameter size of m to 5 mm. In some embodiments, the gas bubbles of the foam have a median diameter size of 0.1 mm to 1 mm. In some embodiments, the gas bubbles of the foam have a median diameter size of 0.1 mm, 0.2 mm, 0.3 mm, 0.4 mm, 0.5 mm, 0.6 mm, 0.7 mm, 0.8 mm, 0.9 mm, or 1 mm, including any value and range therebetween.

In some embodiments, the gas bubbles of the foam have a median diameter size of: 10 μm, 20 μm, 30 μm, 40 μm, or 50 μm, including any value and range therebetween.

The term "diameter" refers to the largest linear distance between two points on the surface of the bubble. The term "diameter", as used herein, may encompass diameters of spherical bubbles as well as of non-spherical bubbles. When referring to multiple gas bubbles, the diameter of the gas bubbles typically refers to the median diameter of the gas bubbles.

As described herein, foam having very small bubbles, for example, in the order of micrometers may be advantageous, as the resulting foam may be stable.

In some embodiments, the liquid foam of the invention has a viscosity of less than 1 Pascal·s (Pa·s), less than 0.1 Pa·s, or less than 0.01 Pa·s. Each possibility represents a separate embodiment of the present invention. In some embodiments, the viscosity of the liquid foam ranges from 0.01 to 1 Pa·s, 0.05 to 1 Pa·s, 0.1 to 1 Pa·s, 0.5 to 1 Pa·s, 0.01 to 0.5 Pa·s, or 0.05 to 0.5 Pa·s. Each possibility represents a separate embodiment of the present invention.

In some embodiments, the liquid foam is characterized by a surface tension (γ) of e.g., 5 mN/m, 10 mN/m, 15 mN/m, 20 mN/m, 25 mN/m, 30 mN/m, 35 mN/m, 40 mN/m, 45 mN/m, or 50 mN/m, including any value and range therebetween.

Typically, but not exclusively, the surface tension may be reduced (e.g., to a value of about 20 mN/m) by incorporating a surfactant within the foam.

In some embodiments, the liquid foam is characterized by of density of 2 to 500 kg/$m^3$. In some embodiments, the liquid foam is characterized by a density of 5 to 500 kg/$m^3$. In some embodiments, the liquid foam is characterized by a density of 5 to 400 kg/$m^3$. In some embodiments, the liquid foam is characterized by a density of 5 to 300 kg/$m^3$. In some embodiments, the liquid foam is characterized by a density of 50 to 200 kg/$m^3$. In some embodiments, the liquid foam is characterized by a density of 50 to 100 kg/$m^3$. In some embodiments, the liquid foam is characterized by a density of 5 to 50 kg/$m^3$. In some embodiments, the liquid foam is characterized by a density of 2, 5, 10, 15, 20, 25, 30, 40, or 50 kg/m·sup.3, including any value and range therebetween.

In some embodiments, the liquid foam may breakdown spontaneously. In some embodiment the liquid foam has a half-life of 0.1 min to 30 min, 0.1 min to 60 min, 0.5 min to 30 min, 0.5 min to 60 min, 1 min to 30 min, or 1 min to 60 min. Each possibility represents a separate embodiment of the present invention. In some embodiments, the indicated half-life is the half-life of the liquid foam within the respiratory system of the subject. In some embodiments, the indicated half-life is the half-life of the liquid foam within the target site. In some embodiments, the half-life range is measured under a temperature range of 35 to 40 degrees Celsius. In some embodiments, the half-life range is measured under a pressure range of 50 to −20 cm$H_2O$ gage.

In some embodiments, ferrofluid (magnetic) foams may be used. In such embodiments, bubble size, flow, and structure may be controlled by altering the magnitude and direction of an externally applied magnetic field.

Active Agents

In some embodiments, the one or more active agents are selected from: therapeutic agent, prophylactic agent and diagnostic agent. In some embodiments, the one or more active agents are selected from, without being limited thereto, a protein, a peptide, a nucleic acid, a small molecule, a lipid, a glycolipid, a cell, and an antibody. In some embodiments, the one or more active agents are selected from, without being limited thereto, a surfactant, a cytotoxic agent, an antineoplastic agent, a chemotherapeutic agent, anti-metastatic agent, a hormone, a steroid, a bronchodilator, an anticoagulant, an immune-modulating agent, a β-agonist, an antibiotic, and an antiviral agent.

In some embodiments, the one or more active agents are selected from, without being limited thereto, therapeutics, vitamins, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, prostaglandins, immunoglobulins, cytokines, and antibodies. Various combinations of these molecules may be used. In some embodiments, the one or more active agents are selected from a protein, a peptide, a nucleic acid, a small molecule, a lipid, a glycolipid, and an antibody.

In some embodiments, the one or more active agents are selected from, without being limited thereto, therapeutic agent, prophylactic agent and diagnostic agent. In some embodiments, the one or more active agents are selected from a cytotoxic agent, an antineoplastic agent, a chemotherapeutic agent, anti-metastatic agent, a hormone, a steroid, a bronchodilator, an anticoagulant, an immunomodulating agent, a β-agonist, an antibacterial agent an antifungal agent, and an antiviral agent.

In some embodiments, the one or more active agents are antimicrobial agents. An "antimicrobial agent" in this context can be an antibacterial agent (antibiotic), an antiviral agent (e.g., zanamivir, and oseltamivir) or an antifungal agent (e.g., Amphotericin B, pentamidine), depending on the source of infection in a subject's body.

In some embodiments the one or more active agents are antibiotics. Non-limiting examples of antibiotics include: cefinetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

In some embodiments the one or more active agents are antihistamines. Non-limiting examples of antihistamines include: azatadine, brompheniramine, chlorpheniramine, clemastine, cyproheptadine, dexmedetomidine, diphenhydramine, doxylamine, hydroxyzine, cetrizine, fexofenadine, loratidine, and promethazine).

Non-limiting examples of chemotherapeutic agents include: Actinomycin, Trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In some embodiments, the one or more active agents are antidiabetic agents. Non-limiting examples of antidiabetic agents include alpha-glucosidase inhibitors, amylin analogs, dipeptidyl peptidase IV inhibitors, incretin mimetics, insulin, meglitinides, non-sulfonylureas, SGLT-2 inhibitors, sulfonylureas, and thiazolidinediones.

In some embodiments, the one or more active agents are anti-cancer therapeutics. For example, chemotherapy and radiotherapy particles may be carried using the foam. Other therapies can also be delivered using the foam, such as vasoconstrictive therapies, which, in some embodiments, may be followed by thermal therapy to locally heat the region. Other possible treatments include delivery of magnetic particles, immunotherapy (such as CAR's) and others. Bringing the anti-cancer therapeutics directly to the tumor site may provide additional benefits for metastasis because such anti-cancer therapeutics may follow the path of the cells that disconnected from the main tumor, into the vascular and lymph circulations.

In some embodiments, the one or more active agents are nucleic acid molecules (e.g., DNA and RNA) for treating various conditions such as treatment of the lung lining for subjects suffering from cystic fibrosis, similar to stem cell treatments for Parkinsons disease (e.g., affecting brain stem), and diabetes (e.g., affecting Islets of Langerhorn). Another drug including genetic material is dornase alpha, marketed under the trademark Pulmozyme™, recombinant DNAse, rhDNase, which is an enzyme used for cystic fibrosis, etc., to reduce the incidence of infection by hydrolyzing DNA in sputum viscoelasticity.

In some embodiment, the active agent is a diagnostic agent. In some embodiment, the diagnostic agent is a contrast-enhancing agent. The term "contrast-enhancing agent" refers to any substance that, when administered to or taken into the body of a human or animal patient, and localized within cells, tissues or organs, may enhance or differentiate those cells, tissues or organs from cells, tissues or organs that have not localized the agent when imaging techniques are used to examine the cells, tissues or organs. For a non-limiting example, the diagnostic agent can be a contrast medium, including e.g. iodine-containing (water-soluble) x-ray-positive contrast media; iodine-containing (water-insoluble) x-ray-positive contrast media; barium containing (water-insoluble) x-ray-positive contrast media; x-ray-negative contrast media; gadolinium compounds, such as e.g. gadolinium DTPA; technetium compounds, such as e.g. compounds containing technetium-99m, for example phosphonates labelled with technetium-99m, Tc-99m-MDP=Tc-99m-methylene-diphosphonate, Tc-99m-tetrofosmin; superparamagnetic iron oxide particles as described above; contrast media which can pass through membranes; enzyme-specific NMR probes, e.g. with paramagnetic dinuclear complexes with lanthanoid ions based on cyclic polyaminopolyacetic acids; glucose contrast media, for example for use in PET (positron emission tomography), including e.g. glucose contrast media coupled to a labelled substance which renders possible external location, e.g. using isotopes which emit positrons, e.g. 18-fluorine, such as, for example, fluoro-2-deoxy-2-D-glucose labelled with 18-fluorine (18FDG), etc. The diagnostic agent can furthermore comprise peptides, proteins, nucleic acids, antibodies, in particular detectable antibodies, low molecular weight detectable compounds, etc.

In some embodiments, there is provided the use of the disclosed foam for washing the lungs. In some embodiments, without being bound by any particular mechanism, when the foam wash is complete, the foam bubbles can be broken leaving much smaller volumes of liquid within the lungs. In some embodiments, the washing is performed using surfactant foam, thus recoating the lungs with the necessary surfactant.

In some embodiments, the invention provides a composition for use in facilitating coating of a target site in a lung. The coating process may be assisted by calculating the dose of an active agent that would cover the airways and not reach the alveoli. That is, when the foam travels it leaves a layer on the airway walls, and the dose reaching the alveoli is all "wasted" on the walls.

Therefore, in some embodiments, the dose may be pre-calculated to avoid such waste. Alternatively, to avoid delivery to the alveoli a push-pull technique, as described herein may be used, i.e. pushing a volume equal to the dead space of the lungs, and then pulling it back leaving just a coating on the airways.

In some embodiments, the active agent is a magnetic element. For a non-limiting example, the inhaled magnetic element may be used in administration of hyperthermia therapy. As used herein "hyperthermia" refers to an induced localized heating at an in vivo site. For example, magnetic nanoparticles can be used to mediate hyperthermia by application of an alternating current field. Conventional alternating current field-based devices such as RF heating, inductive heating, microwave-based procedures, low-field MRI and ultrasound may be used to induce hyperthermia.

Kits

According to some aspects, the invention provides a kit comprising any of the compositions of the invention; and one or more components for the delivery of any of the compositions of the invention, to a first site and/or a target site of the respiratory system. In some embodiments, the kit further comprises a control unit.

In some embodiments, the invention provides a kit comprising any of the liquid foam compositions of the invention; and at a device for administering the liquid foam. In some embodiments, the kit comprises a flow rate limiting mechanism to regulate the flow rate of gas (e.g., air) and/or any of the compositions of the invention.

General

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, “comprise”, “include” and “have” and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein and the laboratory procedures utilized in the present invention include molecular, biochemical, microbiological and recombinant DNA techniques. Such techniques are thoroughly explained in the literature. See, for example, “Molecular Cloning: A laboratory Manual” Sambrook et al., (1989); “Current Protocols in Molecular Biology” Volumes I-III Ausubel, R. M., ed. (1994); Ausubel et al., “Current Protocols in Molecular Biology”, John Wiley and Sons, Baltimore, Maryland (1989); Perbal, “A Practical Guide to Molecular Cloning”, John Wiley & Sons, New York (1988); Watson et al., “Recombinant DNA”, Scientific American Books, New York; Birren et al. (eds) “Genome Analysis: A Laboratory Manual Series”, Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; “Cell Biology: A Laboratory Handbook”, Volumes I-III Cellis, J. E., ed. (1994); “Culture of Animal Cells-A Manual of Basic Technique” by Freshney, Wiley-Liss, N. Y. (1994), Third Edition; “Current Protocols in Immunology” Volumes I-III Coligan J. E., ed. (1994); Stites et al. (eds), “Basic and Clinical Immunology” (8th Edition), Appleton & Lange, Norwalk, CT (1994); Mishell and Shiigi (eds), “Strategies for Protein Purification and Characterization-A Laboratory Course Manual” CSHL Press (1996); “Bacteriophage Methods and Protocols”, Volume 1: Isolation, Characterization, and Interactions, all of which are incorporated by reference. Other general references are provided throughout this document.

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Example 1

Foam Flow Simulations in an Asymmetric Bifurcating Tree Model

An asymmetric bifurcating tree was built, comprising the first seven airway generations, starting at the trachea. This accounts for the region with most pressure loss in the lungs. The geometry is based on a hybrid version of the measurements of Weibel and Horsfield, known in the art. To incorporate the asymmetry of the lung, the bifurcation angles were taken from Horsfield’s data. However, these data are not complete down to the sixth generation in all possible paths, therefore Weibel’s average data were incorporated to complete the picture.

The bifurcation angles for all the branches were taken from Horsfield’s data, while the diameter and branch lengths were taken from Weibel. The exception being the first two generations, for which the lengths were taken from Horsfield in order to incorporate the large scale asymmetry, i.e. between the two lungs.

Figure 2C:
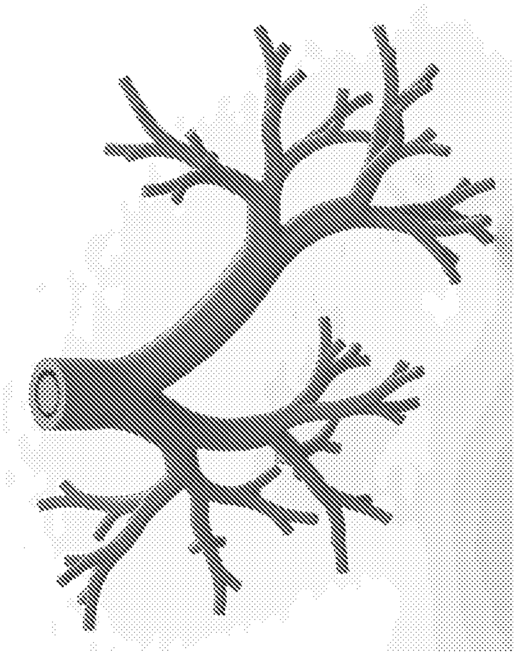
FIGS. 2A-C are front (A) side (B) and trimetric (C) views of an asymmetric bifurcating tree.
Figure 2B:
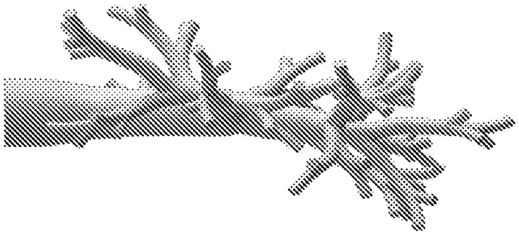
Figure 2A:
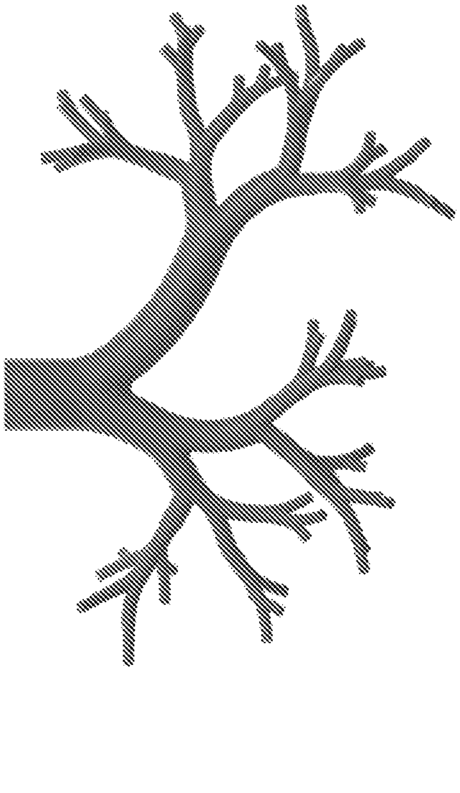

The delivery here is set for an intubated patient. Therefore, in the geometry presented here, the model was truncated at the balloon of the intubation tube. Also, the tube itself was included for more realistic results (FIGS. 2A-C).

Figure 3:
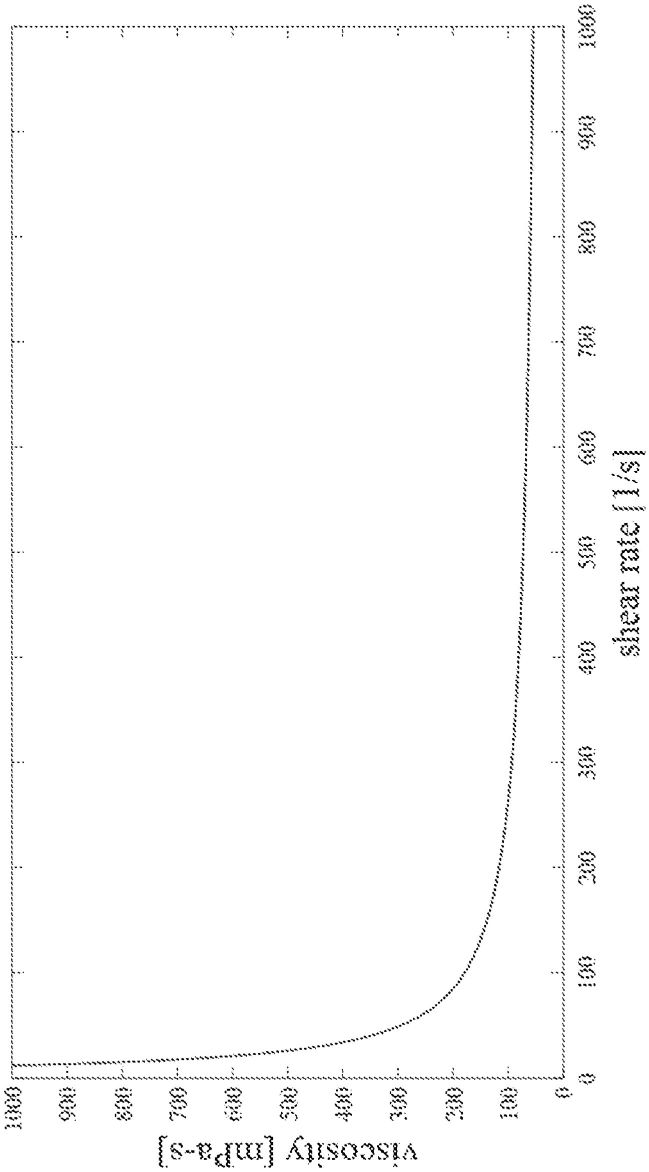
FIG. 3 is a graph showing; Non-Newtonian viscosity with different shear rates (m=0.25 kg/m-s; n=0.75; $\tau$ yield=10 Pa and $\gamma$ critical=0.1 $s^{-1}$)

After rigorous convergence tests, a 2.4M cell mesh with 3 prism layers was selected. Gravity was operating in a direction perpendicular to the trachea, simulating a lying patient. Steady state solver is used. As the Reynolds number is very low, mainly due to the high viscosity, no turbulence modeling is needed. The material density is $\rho=100$ kg/m$^3$. The non-Newtonian viscosity parameters in this case were chosen to be $m=0.25$ kg/m$^{-s}$; $n=0.75$; $\tau_{yield}=10$ Pa and $\gamma_{critical}=0.1$ s$^{-1}$. Using these parameters, depending on the shear rate, the viscosity can have the following values: a flow rate of Q=10 liters/min is prescribed at the inlet (using a velocity inlet boundary condition) and pressure outlet P=0 on all the outlets. The coupled scheme is selected for the pressure-velocity coupling. Least squares cell based, 2$^{nd}$ order and 2$^{nd}$ order upwind is used for the gradients, pressure and momentum, respectively (FIG. 3).

Notably, in this case a flow rate that is beyond the required high end was selected. The viscosity is very high as well, and as can be seen from the FIG. 2, the resulting viscosity is $\mu>100$ mPa·s in most airway regions (e.g., it is noteworthy that water has $\mu=1$ mPa·s and air is =0.02 mPa·s):

With that in mind, the resultant required pressure drop to achieve this flow rate is P=3733 Pa, which is a typical pressure for a ventilation machine known not to cause barotrauma.

Figure 4:
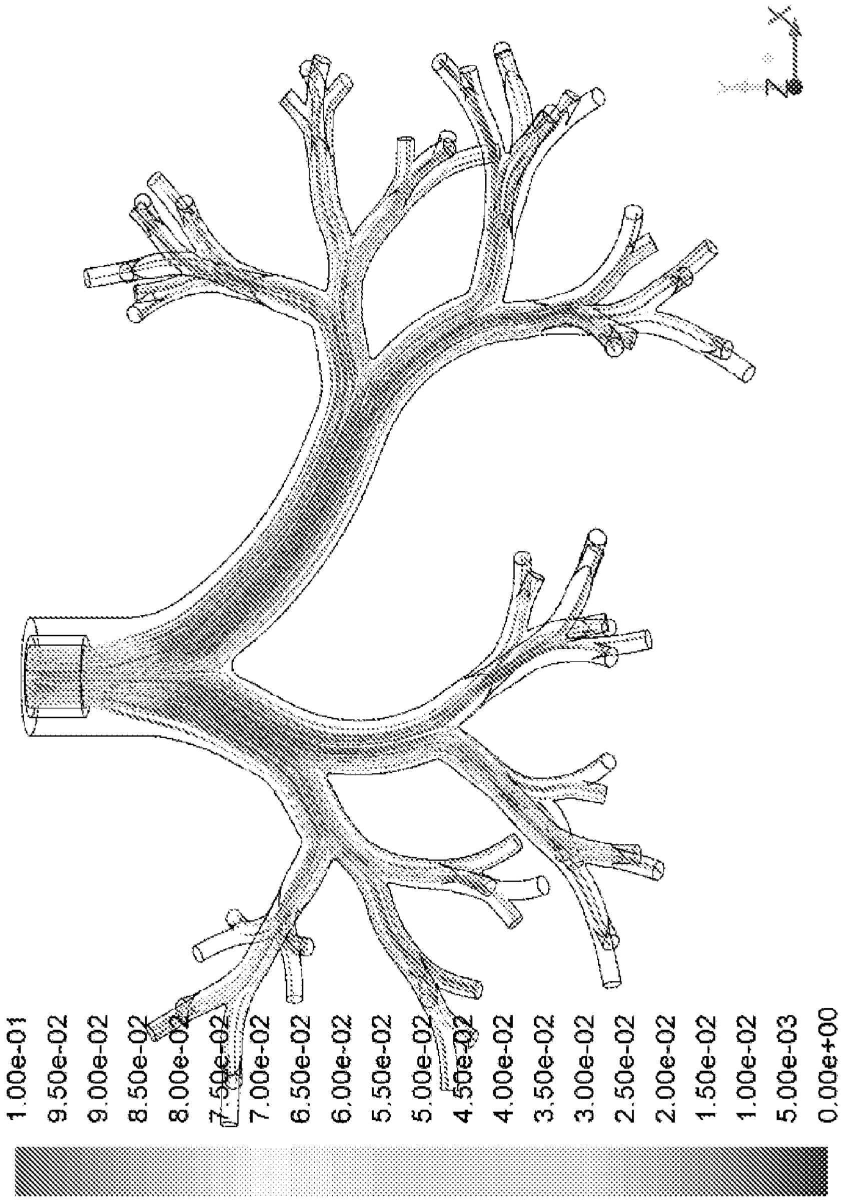
FIG. 4 shows path-lines colored by viscosity [Pa-s]·$\mu$>0.1 Pa-s is colored as $\mu$=0.1 Pa-s.

Finally, FIG. 4 shows that (unlike liquid plugs for example) foam fills the entire airway diameters, and thus it divides well between the lungs, lobes and the different airway branches. Due to the low density of the foam, it is also weakly affected by gravity.

Example 2

Proof of Principal Experiments

Figure 5A:
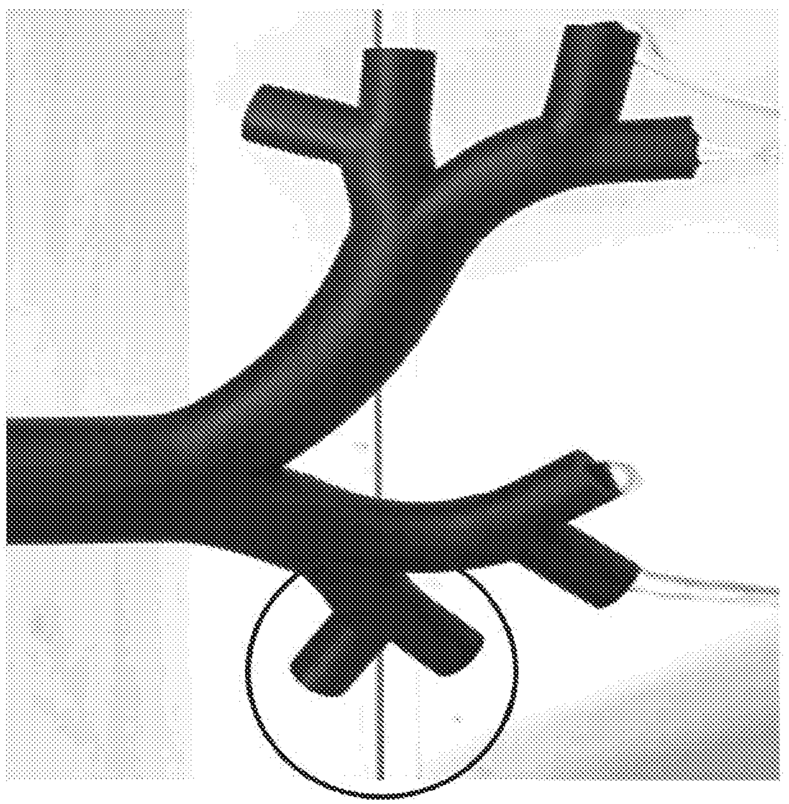
FIGS. 5A-B show a photographic image presenting a proof-of-concept experiment demonstrating the superior distribution of foam in a 3d printed physiological human airway model, showing that while the liquid only exists through the bottom branches (FIG. 5A, circle, right side), the foam is weakly affected by gravity and spreads dramatically more evenly (FIG. 5B, circle, left side)
Figure 5B:
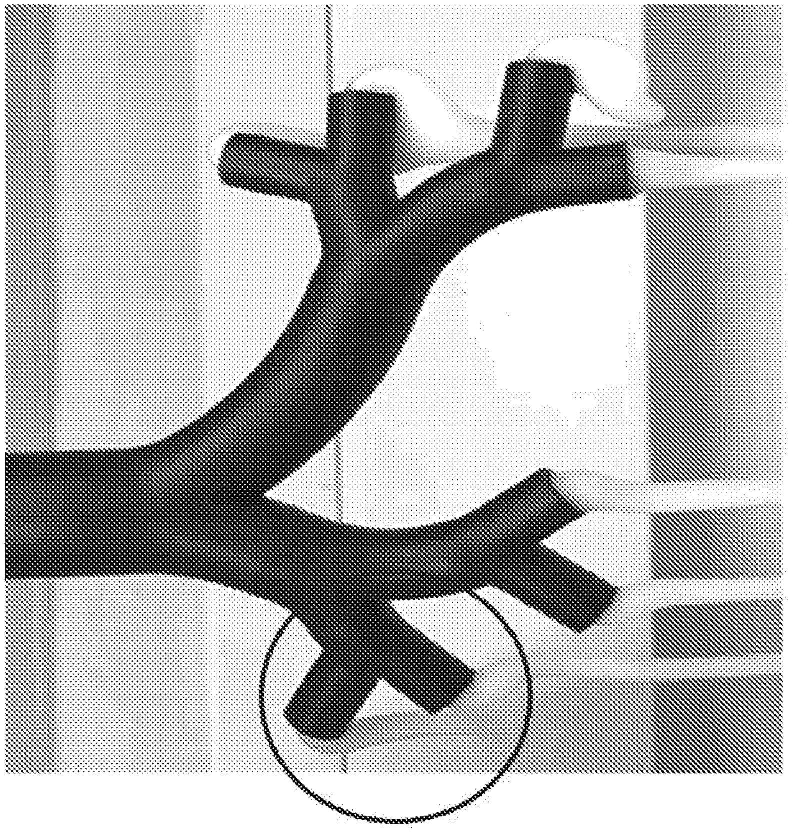

FIGS. 5A-B present an experiment demonstrating the superior distribution of foam in a 3d printed physiological human airway model. While the liquid only exists through the bottom branches (right side, FIG. 5A), the foam is weakly affected by gravity and spreads dramatically more evenly (left side, FIG. 5B).

Figure 7:
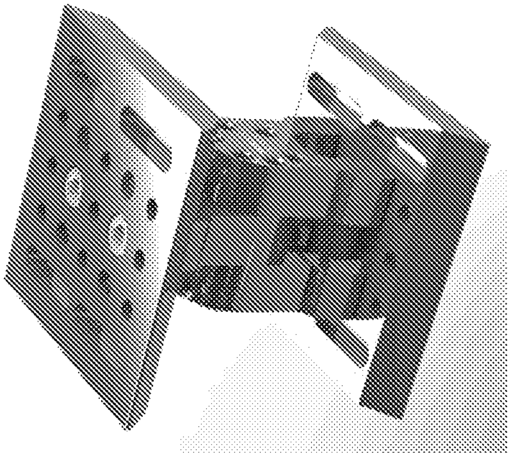
FIG. 7 is a photograph of the tilting table.
Figure 6:
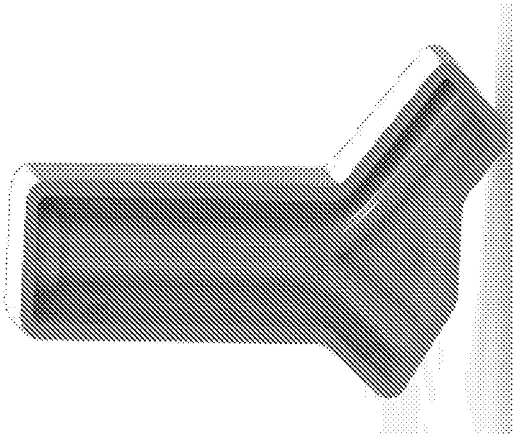
FIG. 6 shows a mold for the airway model.

An experiment to test the feasibility of using foam for pulmonary delivery in a large scale model of the trachea and bronchi, was conducted. FIG. 6 presents a mold for the airway model that was 3d printed together with its mirrored counterpart. The airway model was put on a tilting table presented in FIG. 7. It was put in a way that the trachea (the larger mother branch) is always parallel to the axis of rotation, i.e. always horizontal. For example, a model at 90° corresponds to a situation where the patient is laying on his side.

Figure 8:
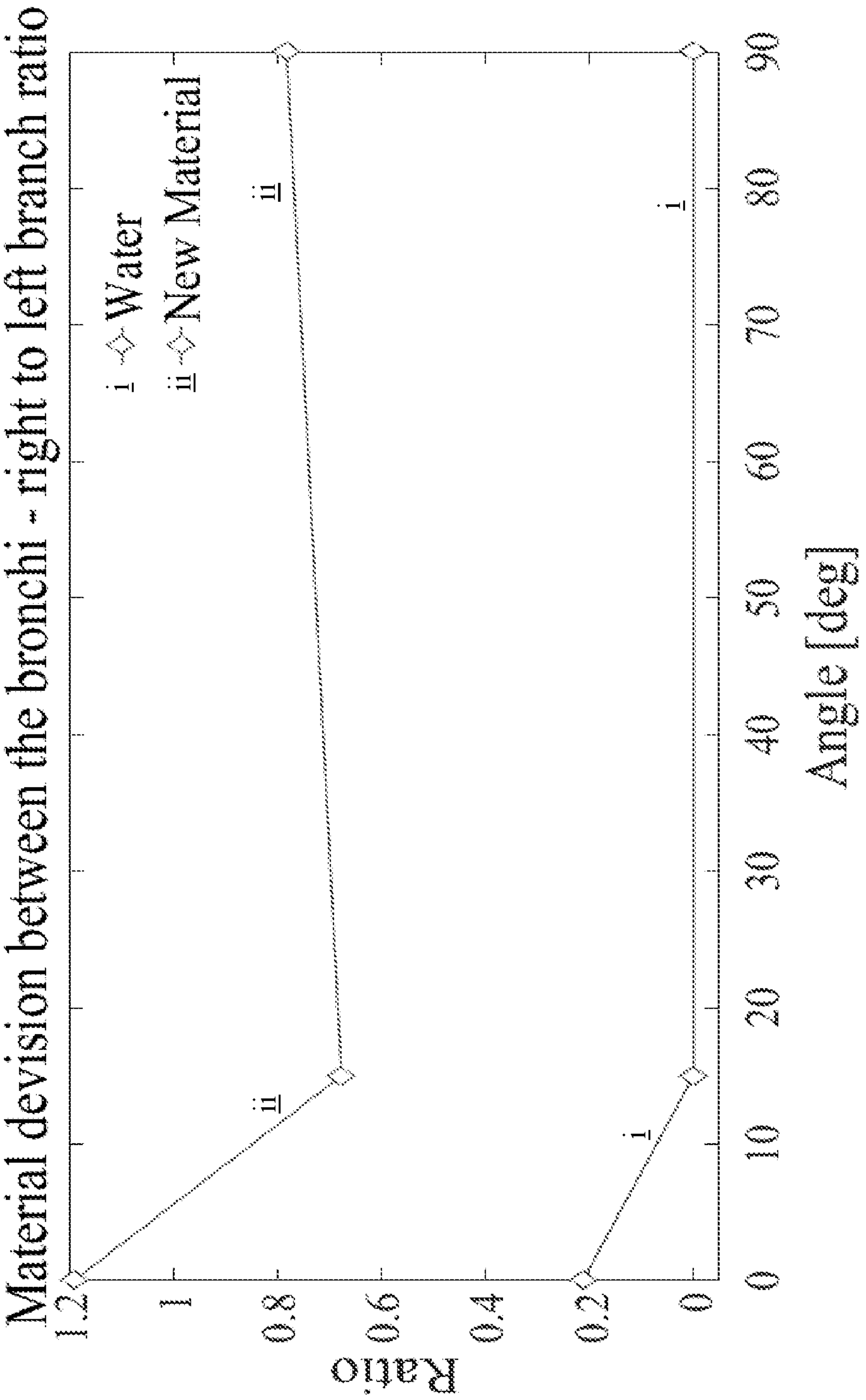
FIG. 8 is a plot demonstrating a ratio of water and foam distribution between the right and left bronchi.

A small straw was inserted into the trachea, and the trachea was blocked around it to prevent backflow of the injected material. This is similar to the balloon at the end of the intubation tube. Water mixed with glycerin 50/50 v/v (Marked as "Water" in FIG. 8) was first injected through the tube into the trachea. After the model was cleaned, foam (Marked as "New Material" in FIG. 8) was injected in the same manner. The foam showed dramatically superior results comparing to a liquid plug (FIG. 8). When the model was not tilted (0 deg angle-representing a person lying on his back) water had flown in a ratio of 0.2 (i.e. ⅕) between the two bronchi (i.e. ratio of drug between left lung and right lung). Once the angle was increased to 15 deg water flowed into one branch and thus into one lung. With the foam on the other hand the ratio was much closer to 1 for all cases (ratio of 1 means equally distributed between the two lungs). Specifically, for a 0 deg angle the ratio was 1.2, and for the most challenging 90 deg position (representing a person lying on his side) the ratio was ~0.8.

Figure 9:
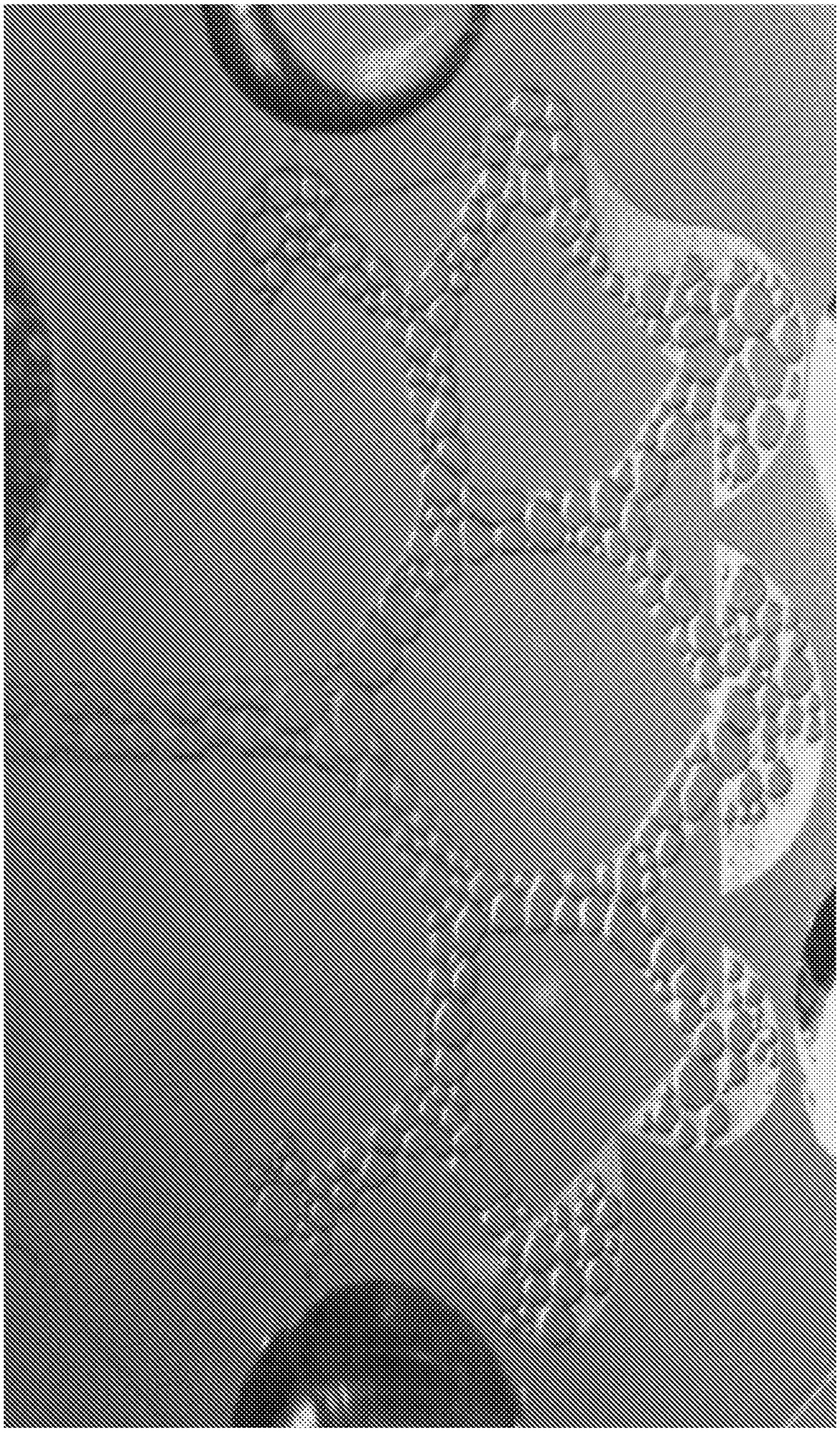
FIG. 9 presents an image showing a snap-shot of foam flow in a microfluidic chip channels' width is roughly 500 m.

Small Scale Model: in exemplary procedures, an experiment was conducted in a microfluidic chip to examine the feasibility of foam flow in such scales. As shown in FIG. 9, the foam divides relatively uniformly.

Example 3

Ex-Vivo Experiment in Pig Lungs

Figure 10:
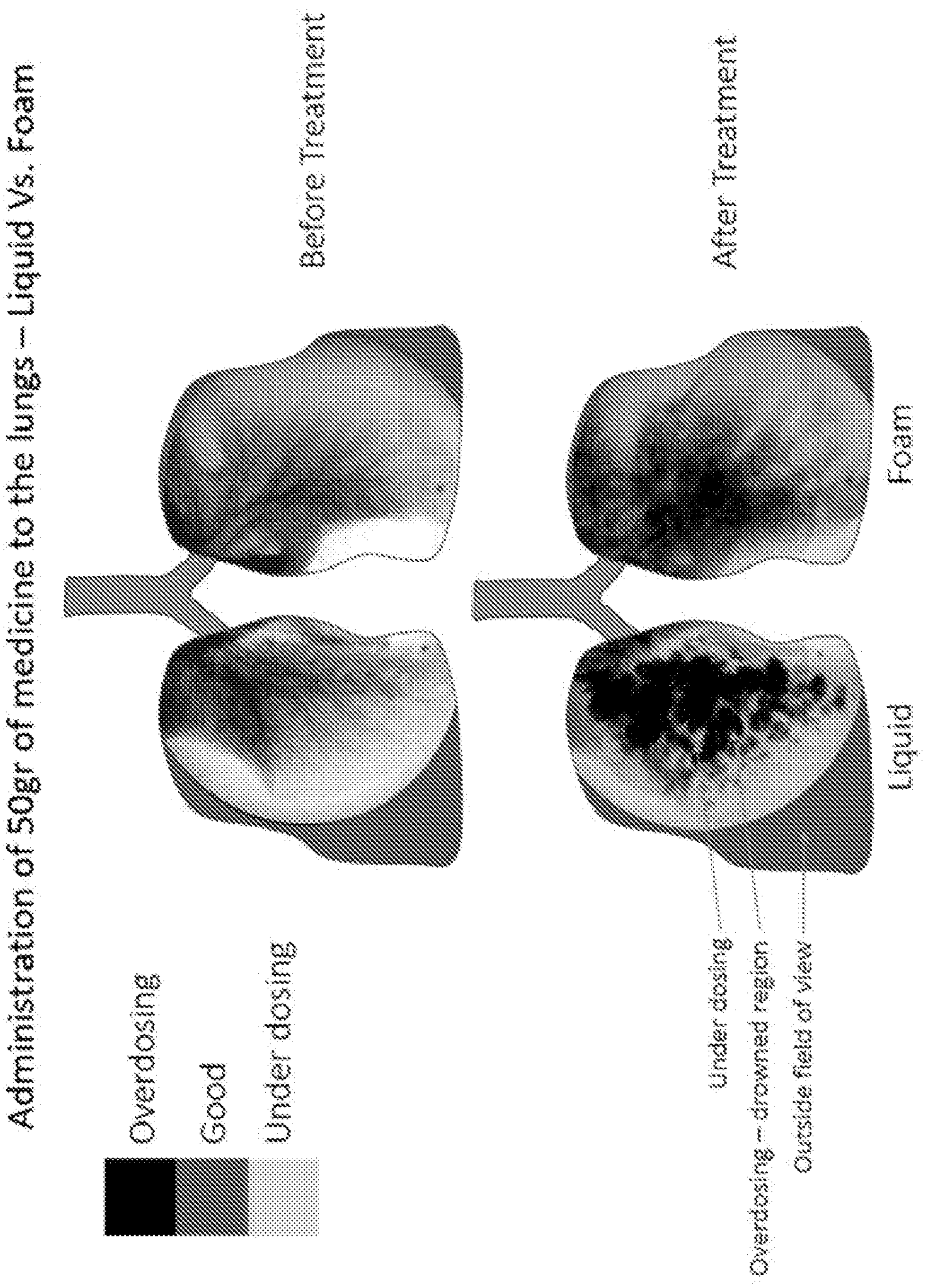
FIG. 10 presents images showing the results of ex-vivo experiment-administration of 50 gr of a medicine to pig's lungs—via a foam vis-á-vis administration via a liquid (upper panel: before treatment, lower panel: after treatment, right side: administration by foam, left side: administration by liquid)

In exemplary procedures, two pig lungs were separated using a double lumen intubation tube. An amount of 50 ml of solution (1% Bovine albumin serum, 49% saline and 50% Urografin) was then administrated to the right lung (left side in FIG. 10). The liquid quickly drained into small pools, visible as black stains as shown in FIG. 10, leaving the regions around these pools and in the distal parts of the lung untreated.

Next, 50 ml of the same solution were then foamed using a mechanical mixer, resulting in roughly 350 ml of stable foam. The foam was then injected into the left lung (right side in FIG. 10), and was spread evenly throughout the lung.

It is noteworthy that in the foam experiments some regions in the middle of the lung are darker than others, mainly in the middle regions of the lung. Without being bound by any particular mechanism, it is assumed that this is mainly due to differences in the out of plane thickness of the lung itself, i.e. the middle part is much thicker than the sides.

Example 4

Live Cell Transport Experiment

Figure 11:
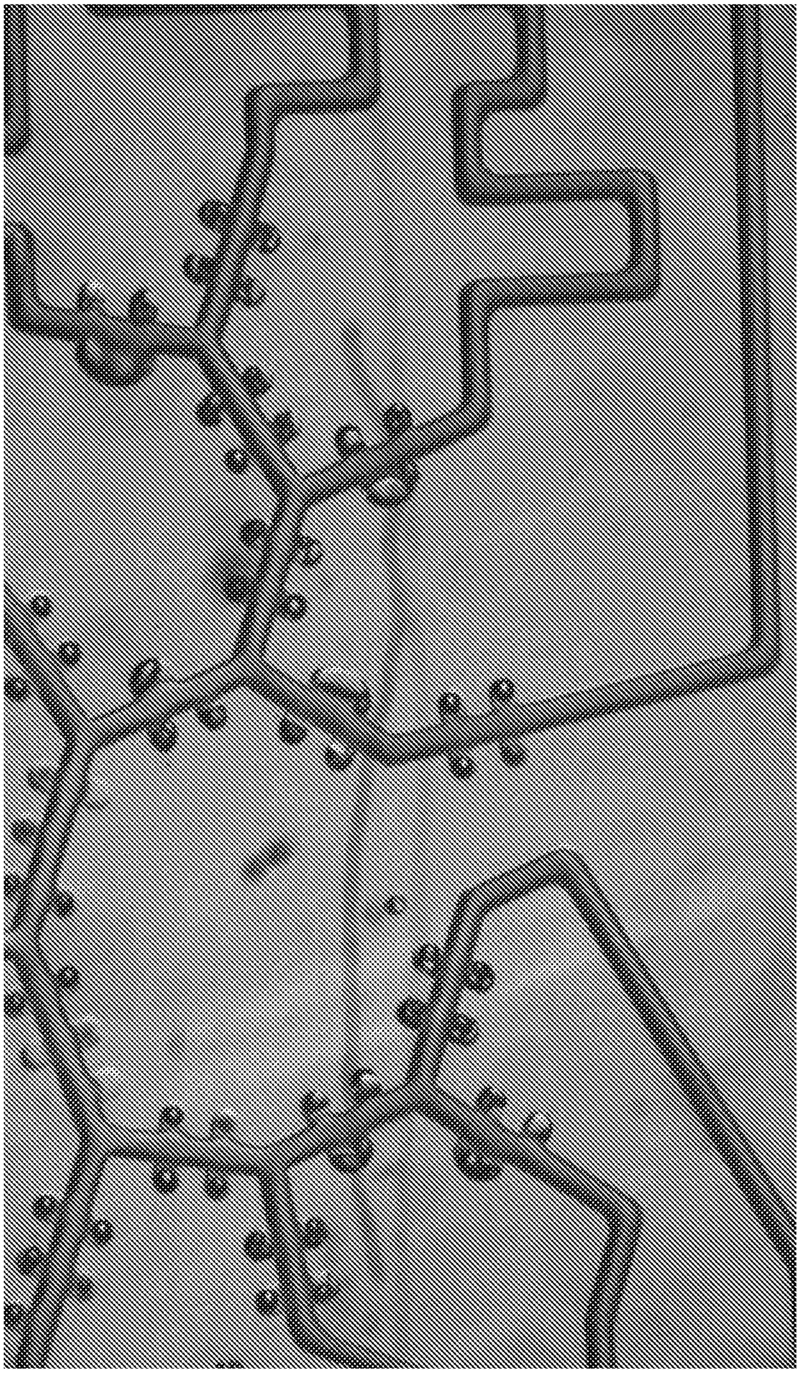
FIG. 11 presents an image showing foamed Roswell Park Memorial Institute (RPMI) 1640 medium mixture, loaded with alveolar type 2 cells, being pushed through a microfluidic chip which mimics alveolar structures in real size (~200 μm) channels.

In exemplary procedures, Roswell Park Memorial Institute (RPMI; 1640, Sigma) cell medium was foamed using a mechanical mixer. Type II alveolar cells were then gently mixed with the foam. This medium and cell mixture was then pushed through a microfluidic chip that mimics alveolar structures in real size ~200 m channels (as shown in FIG. 11).

Figure 12:
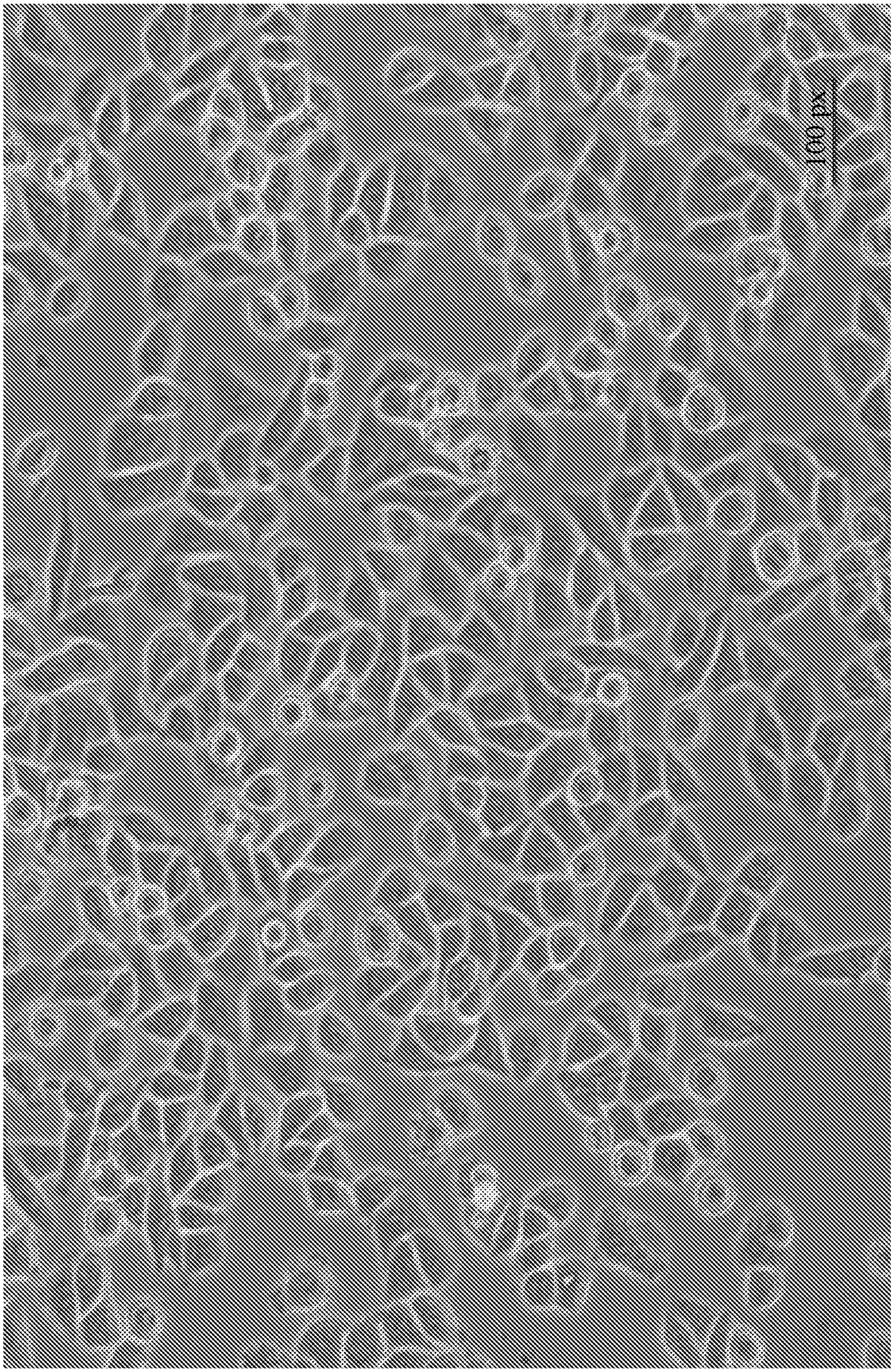
FIG. 12 presents an image showing the mixture (described in FIG. 10) that has left the chip following collecting and put thereof on a petri dish. The Figure shows that the foam slowly broke and the mixture became liquid and that the cells remained alive started creating an epithelial layer on the dish.

The mixture that left the chip was collected and put in a petri dish. The foam slowly broke and the mixture became liquid. The cells remained alive and started creating an epithelial layer in the dish (as shown in FIG. 12).

This experiment proves the feasibility of using foam as a carrier to deliver cells to the lungs, e.g., in the context of stem cell therapy, immunotherapy etc.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method, comprising:
providing a liquid foam;
injecting the liquid foam into an airway of a respiratory system of a patient,
wherein injecting the liquid foam into the airway comprises injecting the liquid foam using at least one of an endotracheal tube, a bronchoscope, a needle, a catheter or an intubation tube;
pushing the liquid foam to a target site within the airway, thereby delivering the liquid foam to the target site and causing the liquid foam to clear the airway at the target site; and
pulling at least a partial amount of the liquid foam out of the airway,
wherein the liquid foam that has been provided, injected, and pulled has a half-life that is in a range of from six seconds to sixty minutes,
wherein the half-life is measured at a temperature of 35 degrees Celsius.

2. The method of claim 1, wherein the target site comprises alveoli.

3. The method of claim 1, wherein the liquid foam comprises a surfactant.

4. The method of claim 1, wherein the liquid foam has a viscosity that is in a range of from 0.01 Pascal-second to 1 Pascal-second.

5. The method of claim 1, wherein the liquid foam has a density that is in a range of from 2 $kg/m^3$ to 500 $kg/m^3$.

6. The method of claim 1, wherein the patient has an obstructive lung disease.

7. A method, comprising:
providing a carrier liquid foam,
wherein the carrier liquid foam comprises an active agent, a therapeutic agent or a diagnosing agent;
injecting the carrier liquid foam into an airway of a respiratory system of a patient,
wherein injecting the carrier liquid foam into the airway comprises injecting the carrier liquid foam using at least one of an endotracheal tube, a bronchoscope, a catheter, a needle, or an intubation tube;

pushing the carrier liquid foam to a target site within the airway, thereby delivering the carrier liquid foam comprising the active agent, the therapeutic agent or the diagnosing agent to the target site, wherein the carrier liquid foam breaks down at the target site, wherein the carrier liquid foam has a half-life that is in a range of from six seconds to sixty minutes, wherein the half-life is measured at a temperature of 35 degrees Celsius.

8. The method of claim 7, wherein pushing the carrier liquid foam to the target site within the airway comprises injecting a volume of gas to thereby push the carrier liquid foam.

9. The method of claim 7, wherein the target site comprises alveoli.

10. The method of claim 7, wherein the carrier liquid foam forms a coating at the target site.

11. The method of claim 7, wherein pushing the carrier liquid foam to the target site comprises pushing the carrier liquid foam within the airway such that the carrier liquid foam does not reach alveoli.

12. The method of claim 11, wherein the carrier liquid foam forms a coating on the airway.

13. The method of claim 12, wherein a dose of the carrier liquid foam is selected so as to cause the carrier liquid foam to form the coating on the airway and so as not to reach the alveoli.

14. The method of claim 7, wherein the carrier liquid foam comprises the active agent, and wherein the active agent comprises an antimicrobial agent, an antibiotic, an antihistamine, a chemotherapeutic agent, an antidiabetic agent, a nucleic acid, a prophylactic agent, a protein, a peptide, a nucleic acid, a small molecule, a lipid, a glycolipid, a cell, an antibody, a cytotoxic agent, an antineoplastic agent, an anti-metastatic agent, a hormone, a steroid, a bronchodilator, an anticoagulant, an immune-modulating agent, a β-agonist, an antifungal agent, an antibacterial agent, an antiviral agent, or combinations thereof.

15. The method of claim 7, wherein the carrier liquid foam comprises the diagnostic agent, and wherein the diagnostic agent comprises a contrast-enhancing agent.

16. The method of claim 7, further comprising:

pulling at least a partial amount of the carrier liquid foam out of the airway, wherein a residual coating of the carrier liquid foam is left at the target site within the airway.

17. The method of claim 7, wherein the carrier liquid foam comprises a surfactant.

18. The method of claim 7, wherein the carrier liquid foam has a viscosity that is in a range of from 0.01 Pascal-second to 1 Pascal-second.

19. A method, comprising:

providing a carrier liquid foam, wherein the carrier liquid foam comprises an active agent, a therapeutic agent or a diagnosing agent:

injecting the carrier liquid foam into an airway of a respiratory system of a patient;

pushing the carrier liquid foam to a target site within the airway, wherein pushing the carrier liquid foam to the target site within the airway comprises injecting a volume of gas to thereby push the carrier liquid foam, thereby delivering the carrier liquid foam comprising the active agent, the therapeutic agent or the diagnosing agent to the target site, wherein the carrier liquid foam breaks down at the target site, wherein the carrier liquid foam has a half-life that is in a range of from six seconds to sixty minutes, wherein the half-life is measured at a temperature of 35 degrees Celsius.

* * * * *